US006916971B1

(12) United States Patent
Cahoon et al.

(10) Patent No.: US 6,916,971 B1
(45) Date of Patent: Jul. 12, 2005

(54) POLYNUCLEOTIDES ENCODING AMINOLEVULINIC ACID BIOSYNTHETIC ENZYMES

(76) Inventors: Rebecca E. Cahoon, 2331 W. 18th St., Wilmington, DE (US) 19806; Steven Gutteridge, 4 Austin Rd., Wilmington, DE (US) 19810; J. Antoni Rafalski, 2028 Longcome Dr., Wilmington, DE (US) 19810

( * ) Notice: Subject to any disclaimer, the term of this patent is extended or adjusted under 35 U.S.C. 154(b) by 185 days.

(21) Appl. No.: 10/018,902

(22) PCT Filed: Jul. 28, 2000

(86) PCT No.: PCT/US00/21008

§ 371 (c)(1),
(2), (4) Date: Dec. 17, 2001

(87) PCT Pub. No.: WO01/09304

PCT Pub. Date: Feb. 8, 2001

Related U.S. Application Data
(60) Provisional application No. 60/146,600, filed on Jul. 30, 1999.

(51) Int. Cl.[7] .......................... A01H 1/00; C07H 21/04; C07K 14/415; C12N 5/14; C12N 9/00

(52) U.S. Cl. ..................... 800/295; 435/6; 435/69.1; 435/468; 435/419; 435/252.3; 435/320.1; 530/370; 536/23.6; 800/278; 800/295

(58) Field of Search ........................ 435/6, 69.1, 70.1, 435/91.4, 468, 183, 410, 419, 252.3, 320.1; 530/370; 536/23.2, 23.6; 800/278, 295

(56) References Cited

U.S. PATENT DOCUMENTS 4,956,282 A * 9/1990 Goodman et al. ....... 435/69.51

FOREIGN PATENT DOCUMENTS

WO 99/29880 A2 6/1999

OTHER PUBLICATIONS

Indu Sangwan et al., Plant Phys., vol. 119:593–598, 1999, Expression of a Soybean Gene Encoding the Tetrapyrrole–Synthesis Enzyme Glutamyl–tRNA Reductase in Symbiotic Root Nodules.
EMBL Database Sequence Listing Accession No AB01141, Mar. 2, 1998, S. Takahashi et al., Cloning of a CDNA Encoding Plastidic Fructose–1,6–Bisphosphatase from Rice.
Dieter Jahn et al., Trends in Biochem. Sciences, vol. 17(6):215–218, 1992, Glutamyl–Transfer RNA: A Precursor of Heme and Chlorophyll Biosynthesis.
Indu Sangwan et al., Plant Phys., vol. 102:829–834, 1993, Expression of the Soybean (*Glycine* max) Glutamate 1–Semialdehyde Aminotransferase Gene in Symbiotic Root Nodules.

Bernhard Grimm et al., PNAS, vol. 87:4169–4173, 1990, Primary Structure of a Key Enzyme in Plant Tetrapyrrole Synthesis: Glutamate 1–Semialdehyde Aminotransferase.

Toru Nakayashiki et al., Plant Phys., vol. 117:332, Plant Gene Register PGR 98–080, Nucleotide Sequence of a CDNA Clone Encoding Glutamyl–tRNA Reductase from Rice, 1998.

National Center for Biotechnology Information General Identifier No. 3913811, Dec. 15, 1998, T. Nakayashiki et al., Nucleotide Sequence of a CDNA Clone Encoding Glutamyl–tRNA Reductase from Rice.

National Center for Biotechnology Information General Identifier No. 1346261, Mar. 1, 2002, R. Tanaka et al., Differential Expression of Two Hema MRNAS Encoding Glutamyl–tRNA Reductase Proteins in Greening Cucumber Seedlings.

Ryouichi Tanaka et al., Plant Phys., vol. 110:1223–1230, 1996, Differential Expression of Two HemA mRNAs Encoding Glutamyl–tRNA Reductase Proteins in Greening Cucumber Seedlings.

National Center for Biotechnology Information General Identifier No. 1039332, Nov. 8, 1996, O. Bougri et al., Members of a Low–Copy Number Gene Family Encoding Glutamyl–tRNA Reductase are Differentially Expressed in Barley.

Oleg Bougri et al., Plant J., vol. 9(6):867–878, 1998, Members of a Low–Copy Number Gene Family Encoding Glutamyl–TRNA Reductase are Differentially Expressed in Barley.

National Center for Biotechnology Information General Identifier No. 4324495, Mar. 3, 1999, I. Sangwan and M. R. O'Brian.

National Center for Biotechnology Information General Identifier No. 1170029, Mar. 1, 2002, B. Grimm et al., Purification and Partial Amino Acid Sequence of the Glutamate 1–Semialdehyde Aminotransferase of Barley and Synechococcus.

(Continued)

*Primary Examiner*—Phuong T. Bui
(74) *Attorney, Agent, or Firm*—Morgan & Finnegan, L.L.P.

(57) ABSTRACT

This invention relates to an isolated nucleic acid fragment encoding an aminolevulinic acid biosynthetic enzyme. The invention also relates to the construction of a chimeric gene encoding all or a portion of the aminolevulinic acid biosynthetic enzyme, in sense or antisense orientation, wherein expression of the chimeric gene results in production of altered levels of the aminolevulinic acid biosynthetic enzyme in a transformed host cell.

10 Claims, 4 Drawing Sheets

OTHER PUBLICATIONS

Bernhard Grimm et al., Carslberg Res. Comm., vol. 54:67–79, 1989, Purification and Partial Amino Acid Sequence of the Glutamate 1–Semialdehyde Aminotransferase of Barley and Synechococcus.

Dieter Jahn et al., Journ. of Biol. Chem., vol. 266(4): 2542–2548, 1991, Two Glutamyl–tRNA Reductase Activities in *Escherichia Coli*.

Dieter Jahn et al., Journ. of Biol. Chem., vol. 266(1): 161–167, 1991, Purification and Functional Characterization of Glutamate–1–Semialdehyde AminoTransferase from Chlamydomonas Reinhardtii.

Jürgen Moser, et al., Methanopyrus kandleri Glutamyl–tRNA Reductase, The Journal of Biological Chemistry, vol. 274, No. 43 of Oct. 22, 1999 pp. 30679–30685.

* cited by examiner

FIGURE 1A

```
                     **   *    *  ******* *          *    * *     *    *    *     *   **  *
SEQ ID NO:04         MATTTSATTAAAAA------ATTAKPRGSSSALCQRVAGGGRR-----RSGVVRCDAAG
SEQ ID NO:12         MAVSTTFSGAKLEALLLKCSSSSSPPPSRSS--FTTFPGQNRRTLIQ--RGVIRCDAQP
SEQ ID NO:29         MAVSTSFPGAKLEALLLKCGSSNAATATATTTHLSCFC-KTRKTLVQSQRGPIRCEASS
                     1                                                         60

*    *    ****** *   ****** *  ******   **********
SEQ ID NO:04         V-EAQAQAVAKAASVAALEQFKISA-DRYMKERSTIAVIGLSVHTAPVEMREKLAVAEEL
SEQ ID NO:12         -SDASSVAPNNATALSALEQLKTSAADRYTKERSSIIAIGLSVHTAPVEMREKLAIPEAE
SEQ ID NO:29         ASDVVADATKKAASVSALEQLKTSAADRYTKERSSVMVIGLSVHSTPVEMREKLAIPEAE
                     61                                                        120

****** ** *********************  **  ** ********   *     *
SEQ ID NO:04         WPRAIQELTSLNHIEEAAVLSTCNRMEIYVVALSWNRGIREVVDWMSKKSGIPASELREH
SEQ ID NO:12         WPRAIAELCSLNHIEEAAVLSTCNRMEIYVLALSQHRGVKEVMEWMSKTSSVPVSELSQH
SEQ ID NO:29         WPRAIAELCSLNHIEEAAVLSTCNRMEIYVVALSKHRGVKEVTEWMSKTSGIPVADLCQH
                     121                                                       180

*  *  ****  * ******************* ****  ****  ** ** *******
SEQ ID NO:04         LFILRSSDATRHLFEVSAGLDSLVLGEGQILAQVKQVVRSGQNSGGLGKNIDRMFKDAIT
SEQ ID NO:12         RFLLYNDATQHLFEVSAGLDSLVLGEGQILSQVKQVVKVGQGVNGFGRNISGLFKHAIT
SEQ ID NO:29         QFLLYNKDATQHLFEVSAGLDSLVLGEGQILAQVKQVVKVGQGVNGFGRNISGLFKHAIT
                     181                                                       240

****** ****  ****    ****  ****************  **********
SEQ ID NO:04         AGKRVRSETNISSGAVSVSSAAVELALMKLPKSEALSARMLLIGAGKMGKLVIKHLVAKG
SEQ ID NO:12         VGKRVRTETNIASGAVSVSSAAVELAYMKLPEASHDNARMLVIGAGKMGKLVIKHLVAKG
SEQ ID NO:29         VGKRVRTETNIAAGAVSVSSAAVELALMKLPEASHANARMLVIGAGKMGKLVIKHLVAKG
                     241                                                       300
```

FIGURE 1B

```
              *  * ******  *** ******  *** ******  ** ** *  * ***  *** ********  ** *
SEQ ID NO:04  CKKVVVVVNRSVERVDAIREEMKDIEIVYRPLSDMYQAAAEADVVFTSTASETSLFAKEHA
SEQ ID NO:12  CKKMVVVVNRTEERVAAIREELKDIEIIYKPLSEMLTCAGEADLVFTSTASENPLFLKEHV
SEQ ID NO:29  CTKMVVVNRSEERVAAIREEIKDVEIIYKPLSEMLTCIGEADVVFTSTASENPLFLKDDV
              301                                                        360

***          ** * * **********  *       ************ **********
SEQ ID NO:04  EALPPVSDTMGGVRLFVDISVPRNVSACVSEVGAARVYNVDDLKEVVEANKEDRLRKAME
SEQ ID NO:12  KDLPPASQEVGGRRFFIDISVPRNVGSCVSDLESVRVYNVDDLKEVVAANKEDRLRKAME
SEQ ID NO:29  KELPPATDEVGGRRLFVDISVPRNVGSCLSDLESVRVYNVDDLKEVVAANKEDRLRKAME
              361                                                        420

** * **     ***********  ********  ***** ** *  **  ** *** ***
SEQ ID NO:04  AQTIITEELRRFEAWRDSLETVPTIKKLRSYADRIRASELEKCLQKVGEDALTKKMRRAI
SEQ ID NO:12  AQAIIAEESKQFEAWRDSLETVPTIKKLRAYAERIRLAELEKCLGKMGDD-IPKKTRRAV
SEQ ID NO:29  AQAIIGEESKQFEAWRDSLETVPTIKKLRAYAERIRLAELEKCLGKMGDD-INKKTQRAV
              421                                                        480

** *********  ********  ****** ********** ** *     ***
SEQ ID NO:04  EELSTGIVNKLLHGPLQHLRCDGSDSRTLDETLENMHALNRMFSLDMEKAIIEQKIKAKV
SEQ ID NO:12  DDLSRGIVNKLLHGPMQHLRCDGNDSRTLSETLENMALNRMFNLETEISVLEEKIRAKV
SEQ ID NO:29  DDLSRGIVNKLLHGPMQHLRCDGSDSRTLSETLENMHALNRMFNLETEISVLEQKIRAKV
              481                                                        540

*
SEQ ID NO:04  EKTQN
SEQ ID NO:12  EQ---
SEQ ID NO:29  EQ-KP
              541
```

FIGURE 2A

```
                    ******  ****   ***  ********  *   *********  *  *******  *  ******
SEQ ID NO:26        MAGAAAASAAAAAVASGISARPVAPRPSPSRARAPRSVVRAAISVEKGEKAYTVEKSEEI
SEQ ID NO:30        MAGAAAA------VASGISIRPVAA-PKISRAPRSRSVVRAAVSID--EKAYTVQKSEEI    60
                    1

********  *******************  *******  ************************
SEQ ID NO:26        FNAAKELMPGGVNSPVRAFKSVGGQPIVFDSVKGSRMWDVDGNEYIDYVGSWGPAIIGHA
SEQ ID NO:30        FNAAKELMPGGVNSPVRAFKSVGGQPIVFDSVKGSHMWDVDGNEYIDYVGSWGPAIIGHA    120
                    61

**  *******************  *******  ***************************  **
SEQ ID NO:26        DDTVNAALIETLKKGTSFGAPCVLENVLAEMVISAVPSIEMVRFVNSGTEACMGALRLVR
SEQ ID NO:30        DDKVNAALIETLKKGTSFGAPCALENVLAQMVISAVPSIEMVRFVNSGTEACMGALRLVR    180
                    121

******  *** *************************  ********  ************
SEQ ID NO:26        AFTGREKILKFEGCYHGHADSFLVKAGSGVATLGLPDSPGVPKGATSETLTAPYNDVEAV
SEQ ID NO:30        AFTGREKILKFEGCYHGHADSFLVKAGSGVATLGLPDSPGVPKGATVGTLTAPYNDADAV    240
                    181

******  * ***************  ********  ************************
SEQ ID NO:26        KKLFEENKGQIAAVFLEPVVGNAGFIPPQPGFLNALRDLTKQDGALLVFDEVMTGFRLAY
SEQ ID NO:30        KKLFEDNKGEIAAVFLEPVVGNAGFIPPQPAFLNALREVTKQDGALLVFDEVMTGFRLAY    300
                    241

*************  **  ****  ************************************
SEQ ID NO:26        GGAQEYFGITPDVSTLGKIIGXGLPVGAYGGRKDIMEMVAPAGPMYQAGTLSGNPLAMTA
SEQ ID NO:30        GGAQEYFGITPDVTTLGKIIGGGLPVGAYGGRKDIMEMVAPAGPMYQAGTLSGNPLAMTA    360
                    301
```

FIGURE 2B

```
              ********************* **** ** ****** ** ******************************* *******
SEQ ID NO:26  GIHTLKRLMEPGTYDYLDKITGDLVRGVLDAGAKTGHEMCGGHIRGMFGFFFTAGPVHNF
SEQ ID NO:30  GIHTLKRLMEPGTYEYLDKVTGELVRGILDVGAKTGHEMCGGHIRGMFGFFFAGGPVHNF
              361                                                        420

********************* **** ****************** **********  ****    *
SEQ ID NO:26  GDAKKSDTAKFGRFYRGMLEEGVYLAPSQFEAGFTSLAHTSQDIEKTVEAAAKVLRRI
SEQ ID NO:30  DDAKKSDTAKFGRFHRGMLGEGVYLAPSQFEAGFTSLAHTTQDIEKTVEAAEKVLRWI
              421                                                       478
```

POLYNUCLEOTIDES ENCODING AMINOLEVULINIC ACID BIOSYNTHETIC ENZYMES

This application claims the benefit of U.S. Provisional Application No. 60/146,600, filed Jul. 30, 1999.

FIELD OF THE INVENTION

This invention is in the field of plant molecular biology. More specifically, this invention pertains to nucleic acid fragments encoding aminolevulinic acid biosynthetic enzymes in plants and seeds.

BACKGROUND OF THE INVENTION

A major regulatory point in the biosynthesis of tetrapyrrolic pigments like chlorophyll and heme is the formation of the building block 5-aminolevulinic acid (ALA) which provides all the carbon and nitrogen atoms of the tetrapyrrole ring. There are two different routes by which ALA is synthesized in the living cell. In animals, fungi and some eubacteria, succinyl-CoA and glycine are condensed by ALA synthase to yield ALA with the concomitant liberation of the carboxyl carbon of glycine as carbon dioxide. In contrast, in plants, algae and certain eubacteria, ALA is formed from Glu-tRNA$^{Glu}$ via two enzymatic reactions (Jahn et al. (1992) *Trends Biochem Sci* 17:215–218). First, Glu-tRNA reductase converts Glu-tRNA$^{Glu}$ to glutamate 1-semialdehyde (GSA) with the concomitant release of tRNA$^{Glu}$. GSA aminotransferase then converts GSA to ALA.

Given the facts that plants and animals differ in the way they synthesize ALA and that ALA is an essential compound for survival, it is envisioned that inhibitors of Glu-tRNA reductase and GSA aminotransferase may serve as effective herbicides that are nontoxic to man and other animals. Genes encoding Glu-tRNA reductase and GSA aminotransferase may be isolated and then overexpressed in bacterial or yeast hosts to provide the huge amounts of protein that is needed for inhibitor discovery and design.

SUMMARY OF THE INVENTION

The present invention concerns an isolated polynucleotide comprising a nucleotide sequence selected from the group consisting of: (a) a first nucleotide sequence encoding a polypeptide of at least 25 amino acids having at least 80% identity based on the Clustal method of alignment when compared to a polypeptide of SEQ ID NO:18; (b) a second nucleotide sequence encoding a polypeptide of at least 25 amino acids having at least 85% identity based on the Clustal method of alignment when compared to a polypeptide of SEQ ID NO:10; (c) a third nucleotide sequence encoding a polypeptide of at least 40 amino acids having at least 85% identity based on the Clustal method of alignment when compared to a polypeptide of SEQ ID NO:14; (d) a fourth nucleotide sequence encoding a polypeptide of at least 50 amino acids having at least 80% identity based on the Clustal method of alignment when compared to a polypeptide of SEQ ID NO:28; (e) a fifth nucleotide sequence encoding a polypeptide of at least 50 amino acids having at least 90% identity based on the Clustal method of alignment when compared to a polypeptide of SEQ ID NO:24; (f) a sixth nucleotide sequence encoding a polypeptide of at least 50 amino acids having at least 95% identity based on the Clustal method of alignment when compared to a polypeptide of SEQ ID NO:2; (g) a seventh nucleotide sequence encoding a polypeptide of at least 80 amino acids having at least 95% identity based on the Clustal method of alignment when compared to a polypeptide of SEQ ID NO:6; (h) an eighth nucleotide sequence encoding a polypeptide of at least 240 amino acids having at least 90% identity based on the Clustal method of alignment when compared to a polypeptide of SEQ ID NO:22; (i) a ninth nucleotide sequence encoding a polypeptide of at least 250 amino acids having at least 80% identity based on the Clustal method of alignment when compared to a polypeptide of SEQ ID NO:16; (j) a tenth nucleotide sequence encoding a polypeptide of at least 300 amino acids having at least 95% identity based on the Clustal method of alignment when compared to a polypeptide selected from the group consisting of SEQ ID NOs:4 and 26; (k) an eleventh nucleotide sequence encoding a polypeptide of at least 500 amino acids having at least 90% identity based on the Clustal method of alignment when compared to a polypeptide of SEQ ID NO:12; and (l) a twelfth nucleotide sequence comprising the complement of (a), (b), (c), (d), (e), (f), (g), (h), (i), G) or (k).

In a second embodiment, it is preferred that the isolated polynucleotide of the claimed invention comprises a first nucleotide sequence which comprises a nucleic acid sequence selected from the group consisting of SEQ ID NOs:1, 3, 5, 9, 11, 13, 15, 17, 21, 23, 25, and 27 that codes for the polypeptide selected from the group consisting of SEQ ID NOs:2, 4, 6, 10, 12, 14, 16, 18, 22, 24, 26, and 28.

In a third embodiment, this invention concerns an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 9, 11, 13, 15, 17, 21, 23, 25, and 27 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

In a seventh embodiment, the invention concerns a Glu-tRNA reductase or GSA aminotransferase polypeptide selected from the group consisting of: (a) a polypeptide of at least 25 amino acids having at least 80% identity based on the Clustal method of alignment when compared to a polypeptide of SEQ ID NO:18; (b) a polypeptide of at least 25 amino acids having at least 85% identity based on the Clustal method of alignment when compared to a polypeptide of SEQ ID NO:10; (c) a polypeptide of at least 40 amino acids having at least 85% identity based on the Clustal method of alignment when compared to a polypeptide of SEQ ID NO:14; (d) a polypeptide of at least 50 amino acids having at least 80% identity based on the Clustal method of alignment when compared to a polypeptide of SEQ ID NO:28; (e) a polypeptide of at least 50 amino acids having at least 90% identity is based on the Clustal method of alignment when compared to a polypeptide of SEQ ID NO:24; (f) a polypeptide of at least 50 amino acids having at least 95% identity based on the Clustal method of alignment when compared to a polypeptide of SEQ ID NO:2; (g) a polypeptide of at least 80 amino acids having at least 95% identity based on the Clustal method of alignment when compared to a polypeptide of SEQ ID NO:6; (h) a polypeptide of at least 240 amino acids having at least 900/c identity based on the Clustal method of alignment when compared to a polypeptide of SEQ ID NO:22; (i) a polypeptide of at least 250 amino acids having at least 80% identity based on the Clustal method of alignment when compared to a polypeptide of SEQ ID NO:16; (j) a polypeptide of at least 300 amino acids having at least 95% identity based on the Clustal method of alignment when compared to a polypeptide selected from the group consisting of SEQ ID NOs:4 and 26; and (k) a polypeptide of at least 500 amino acids having at least 90% identity based on the Clustal method of alignment when compared to a polypeptide of SEQ ID NO:12.

In an eighth embodiment, the invention relates to a method of selecting an isolated polynucleotide that affects the level of expression of a Glu-tRNA reductase or a GSA aminotransferase polypeptide or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the Glu-tRNA reductase or a GSA aminotransferase polypeptide or enzyme activity in the host cell containing the isolated polynucleotide; and (d) comparing the level of the Glu-tRNA reductase or a GSA aminotransferase polypeptide or enzyme activity in the host cell containing the isolated polynucleotide with the level of the Glu-tRNA reductase or a GSA aminotransferase polypeptide or enzyme activity in the host cell that does not contain the isolated polynucleotide.

In a ninth embodiment, the invention concerns a method of obtaining a nucleic acid fragment encoding a substantial portion of a Glu-tRNA reductase or a GSA aminotransferase polypeptide, preferably a plant Glu-tRNA reductase or a GSA aminotransferase polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 9, 11, 13, 15, 17, 21, 23, 25, and 27 and the complement of such nucleotide sequences; and amplifying a nucleic acid fragment (preferably a cDNA inserted in a cloning vector) using the oligonucleotide primer. The amplified nucleic acid fragment preferably will encode a substantial portion of a Glu-tRNA reductase or a GSA aminotransferase amino acid sequence.

In a tenth embodiment, this invention relates to a method of obtaining a nucleic acid fragment encoding all or a substantial portion of the amino acid sequence encoding a Glu-tRNA reductase or a GSA aminotransferase polypeptide comprising the steps of: probing a cDNA or genomic library with an isolated polynucleotide of the present invention; iv identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide of the present invention.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the Glu-tRNA reductase or the GSA aminotransferase polynucleotide in an amount sufficient to complement a null mutant to provide a positive selection means.

In a thirteenth embodiment, this invention relates to a method of altering the level of expression of an aminolevulinic acid biosynthetic enzyme in a host cell comprising: (a) transforming a host cell with a chimeric gene of the present invention; and (b) growing the transformed host cell under conditions that are suitable for expression of the chimeric gene wherein expression of the chimeric gene results in production of altered levels of the aminolevulinic acid biosynthetic enzyme in the transformed host cell.

A further embodiment of the instant invention is a method for evaluating at least one compound for its ability to inhibit the activity of an aminolevulinic acid biosynthetic enzyme, the method comprising the steps of: (a) transforming a host cell with a chimeric gene comprising a nucleic acid fragment encoding an aminolevulinic acid biosynthetic enzyme polypeptide, operably linked to suitable regulatory sequences; (b) growing the transformed host cell under conditions that are suitable for expression of the chimeric gene wherein expression of the chimeric gene results in production of an aminolevulinic acid biosynthetic enzyme in the transformed host cell; (c) optionally purifying the aminolevulinic acid biosynthetic enzyme polypeptide expressed by the transformed host cell; (d) treating the aminolevulinic acid biosynthetic enzyme polypeptide with a compound to be tested; and (e) comparing the activity of the aminolevulinic acid biosynthetic enzyme polypeptide that has been treated with a test compound to the activity of an untreated aminolevulinic acid biosynthetic enzyme polypeptide, thereby selecting compounds with potential for inhibitory activity.

BRIEF DESCRIPTION OF THE DRAWINGS AND SEQUENCE LISTING

The invention can be more fully understood from the following detailed description and the accompanying drawings and Sequence Listing which form a part of this application.

FIGS. 1A–1B present an alignment of amino acid sequences of Glu-tRNA reductase encoded by the nucleotide sequences derived from corn clone csc1c.pk005.i15 (SEQ ID NO:4) and soybean clone sfl1.pk0060.c4 (SEQ ID NO:12), and the Glu-tRNA reductase from *Glycine max* (NCBI GI No. 4324495; SEQ ID NO:29). Amino acids which are conserved among all and at least two sequences with an amino acid at that position are indicated with an asterisk (*). Dashes are used by the program to maximize alignment of the sequences.

FIGS. 2A–2B present an alignment of amino acid sequences of GSA aminotransferase encoded by the nucleotide sequence derived from rice clone rl0n.pk0078.b9 (SEQ ID NO:26) and the GSA aminotransferase from *Hordeum*

*vulgare* (NCBI GI No. 1170029; SEQ ID NO:30). Amino acids which are conserved between the two sequences are indicated with an asterisk (*). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig*"), contigs assembled from an FIS and one or more ESTs ("Contig*"), or sequences encoding the entire protein derived from an FIS, a contig, or an FIS and PCR ("CGS"). Nucleotide SEQ ID NOs:1, 5, 9, 13, 17, 23, and 27 correspond to nucleotide SEQ ID NOs:1, 3, 5, 7, 9, 13, and 17, respectively, presented in U.S. Provisional Application No. 60/146,600, filed Jul. 30, 1999. Amino acid SEQ ID NOs:2, 6, 10, 14, 18, 24, and 28 correspond to amino acid SEQ ID NOs:2, 4, 6, 8, 10, 14, and 18, respectively, presented in U.S. Provisional Application No. 60/146,600, filed Jul. 30, 1999. The sequence descriptions and Sequence Listing attached hereto comply with the rules governing nucleotide and/or amino acid sequence disclosures in patent applications as set forth in 37 C.F.R §1.821–1.825.

TABLE 1

Aminolevulinic Acid Biosynthetic Enzymes

| Protein (Plant Source) | Clone Designation | Status | SEQ ID NO: (Nucleotide) | SEQ ID NO: (Amino Acid) |
|---|---|---|---|---|
| Glu-tRNA Reductase (Corn) | p0008.cb3lk05r | EST | 1 | 2 |
| Glu-tRNA Reductase (Corn) | csclc.pk005.i15 | CGS (FIS) | 3 | 4 |
| Glu-tRNA Reductase (Rice) | rlr48.pk0037.f4 | EST | 5 | 6 |
| Glu-tRNA Reductase (Rice) | rlr48.pk0037.f4 | FIS | 7 | 8 |
| Glu-tRNA Reductase (Soybean) | sfl1.pk0060.c4 | EST | 9 | 10 |
| Glu-tRNA Reductase (Soybean) | sfl1.pk0060.c4 | CGS (FIS) | 11 | 12 |
| Glu-tRNA Reductase (Soybean) | srr1c.pk001.p10 | EST | 13 | 14 |
| Glu-tRNA Reductase (Soybean) | srr1c.pk001.p10 | FIS | 15 | 16 |
| Glu-tRNA Reductase (Soybean) | ses8w.pk0017.c6 | EST | 17 | 18 |
| Glu-tRNA Reductase (Wheat) | wlln.pk0060.b11 | FIS | 19 | 20 |
| GSA Aminotransferase (Corn) | cr1.pk0013.e7 | FIS | 21 | 22 |
| GSA Aminotransferase (Rice) | r10n.pk0078.b9 | EST | 23 | 24 |
| GSA Aminotransferase (Rice) | r10n.pk0078.b9 | CGS (FIS) | 25 | 26 |
| GSA Aminotransferase (Wheat) | wlm12.pk0015.d7 | EST | 27 | 28 |

The Sequence Listing contains the one letter code for nucleotide sequence characters and the three letter codes for amino acids as defined in conformity with the IUPAC-IUBMB standards described in Nucleic Acids Res. 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 9, 11, 13, 15, 17, 21, 23, 25, and 27, or the complement of such sequences.

The term "isolated" polynucleotide refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terns "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 9, 11, 13, 15, 17, 21, 23, 25, and 27 and the complement of such nucleotide sequences may be used in methods of selecting an isolated polynucleotide that affects the expression of a Glu-tRNA reductase or a GSA aminotransferase polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min. and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2X SSC, 0.5% SDS was increased to 60° C. Another preferred set of highly stringent conditions uses two final washes in 0.1X SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 25, 40, or 50 amino acids, preferably at least 80 or 100 amino acids, more preferably at least 150 amino acids, still more preferably at least 200 amino acids, and most preferably at least 240, 250, 300, or 500 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide, Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to con the entire desired nucleic acid fragment "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' noncoding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Kienow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' noncoding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function "Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) Meth Enzymol. 143:277) and particle-accelerated or "gene gun" transformation technology (Klein et al. (1987) Nature (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. Molecular Cloning: A Laboratory Manual; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) a first nucleotide sequence encoding a polypeptide of at least 25 amino acids having at least 80% identity based on the Clustal method of alignment when compared to a polypeptide of SEQ ID NO:18; (b) a second nucleotide sequence encoding a polypeptide of at least 25 amino acids having at least 85% identity based on the Clustal method of alignment when compared to a polypeptide of SEQ ID NO:10; (c) a third nucleotide sequence encoding a polypeptide of at least 40 amino acids having at least 85% identity based on the Clustal method of alignment when compared to a polypeptide of SEQ ID NO:14; (d) a fourth nucleotide sequence encoding a polypeptide of at least 50 amino acids having at least 80% a identity based on the Clustal method of alignment when compared to a polypeptide of SEQ ID NO:28; (e) a fifth nucleotide sequence encoding a polypeptide of at least 50 amino acids having at least 90% identity based on the Clustal method of alignment when compared to a polypeptide of SEQ ID NO:24; (f) a sixth nucleotide sequence encoding a polypeptide of at least 50 amino acids having at least 95% identity based on the Clustal method of alignment when compared to a polypeptide of SEQ ID NO:2; (g) a seventh nucleotide sequence encoding a polypeptide of at least 80 amino acids having at least 95% identity based on the Clustal method of alignment when compared to a polypeptide of SEQ ID NO:6; (h) an eighth nucleotide sequence encoding a polypeptide of at least 240 amino acids having at least 90% identity based on the Clustal method of alignment when compared to a polypeptide of SEQ ID NO:22; (i) a ninth nucleotide sequence encoding a polypeptide of at least 250 amino acids having at least 80% identity based on the Clustal method of alignment when compared to a polypeptide of SEQ ID NO:16; (j) a tenth nucleotide sequence encoding a polypeptide of at least 300 amino acids having at least 95% identity based on the Clustal method of alignment when compared to a polypeptide selected from the group consisting of SEQ ID NOs:4 and 26; (k) an eleventh nucleotide sequence encoding a polypeptide of at least 500 amino acids having at least 90% identity based on the Clustal method of alignment when compared to a polypeptide of SEQ ID NO:12; and (l) a twelfth nucleotide sequence comprising the complement of (a), (b), (c), (d), (e), (f), (g), (h), (i), (j) or (k).

Preferably, the first nucleotide sequence comprises a nucleic acid sequence selected from the group consisting of SEQ ID NOs:1, 3, 5, 9, 11, 13, 15, 17, 21, 23, 25, and 27, that codes for the polypeptide selected from the group consisting of SEQ ID NOs:2, 4, 6, 10, 12, 14, 16, 18, 22, 24, 26, and 28.

Nucleic acid fragments encoding at least a portion of several aminolevulinic acid biosynthetic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other Glu-tRNA reductase or a GSA aminotransferase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci.* USA 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad Sci.* USA 86:5673–5677; Loh et al. (1989) *Science* 243:217–220). Products generated by the 3' and 5' RACE procedures can be combined to generate fill-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 9, 11, 13, 15, 17, 21, 23, 25, and 27 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a Glu-tRNA reductase or a GSA aminotransferase polypeptide, preferably a substantial portion of a plant Glu-tRNA reductase or a GSA aminotransferase polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 9, 11, 13, 15, 17, 21, 23, 25, and 27, and the complement of such nucleotide sequences; and amplifying a nucleic acid fragment (preferably a cDNA inserted in a cloning vector) using the oligonucleotide primer. The amplified nucleic acid fragment preferably will encode a portion of a Glu-tRNA reductase or a GSA aminotransferase polypeptide.

Availability of the instant nucleotide and deduced amino acid sequences facilitates immunological screening of cDNA expression libraries. Synthetic peptides representing portions of the instant amino acid sequences may be synthesis. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment this invention concerns viruses and host cells comprising either the chimeric genes of the invention as described herein or an isolated polynucleotide of the invention as described herein. Examples of host cells which can be used to practice the invention include, but are not limited to, yeast bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of tetrapyrrolic pigments like heme and chlorophyll in those cells. The nucleic acid fragments of the instant invention may also be used for overexpression in bacterial or yeast hosts, thereby efficiently producing large amounts of the encoded polypeptides which could then be used for screening different compounds for potential herbicidal activity.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Noncoding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intercellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the cosuppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dormant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide selected from the group consisting of: (a) a polypeptide of at least 25 amino acids having at least 80% identity based on the Clustal method of alignment when compared to a polypeptide of SEQ ID NO:18; (b) a polypeptide of at least 25 amino acids having at least 85% identity based on the Clustal method of alignment when compared to a polypeptide of SEQ ID NO:10; (c) a polypeptide of at least 40 amino acids having at least 85% identity based on the Clustal method of alignment when compared to a polypeptide of SEQ ID NO:14; (d) a polypeptide of at least 50 amino acids having at least 80% identity based on the Clustal method of alignment when compared to a polypeptide of SEQ ID NO:28; (e) a polypeptide of at least 50 amino acids having at least 90% identity based on the Clustal method of alignment when compared to a polypeptide of SEQ ID NO:24; (f) a polypeptide of at least 50 amino acids having at least 95% identity based on the Clustal method of alignment when compared to a polypeptide of SEQ ID NO:2; (g) a polypeptide of at least 80 amino acids having at least 95% identity based on the Clustal method of alignment when compared to a polypeptide of SEQ ID NO:6; (h) a polypeptide of at least 240 amino acids having at least 90% identity based on the Clustal method of alignment when compared to a polypeptide of SEQ ID NO:22; (i) a polypeptide of at least 250 amino acids having at least 80% identity based on the Clustal method of alignment when compared to a polypeptide of SEQ ID NO:16; (j) a polypeptide of at least 300 amino acids having at least 95% identity based on the Clustal method of alignment when compared to a polypeptide selected from the group consisting of SEQ ID NOs:4 and 26; and k a polypeptide of at least 500 amino acids having at least 90% identity based on the Clustal method of alignment when compared to a polypeptide of SEQ ID NO:12.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded aminolevulinic acid biosynthetic enzyme. An example of a vector for high level expression of the instant polypeptides in a bacterial host is provided (Example 7).

Additionally, the instant polypeptides can be used as a target to facilitate design and/or identification of inhibitors of those enzymes that may be useful as herbicides. This is desirable because the polypeptides described herein catalyze various steps in aminolevulinic acid biosynthesis. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hun. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Karazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:679–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries: Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| cr1 | Corn Root From 7 Day Old Seedlings | cr1.pk0013.e7 |
| csc1c | Corn 20 Day Old Seedling (Germination Cold Stress) | csc1c.pk005.i15 |
| p0008 | Corn 3 Week Old Leaf | p0008.cb3lk05r |
| rl0n | Rice 15 Day Old Leaf* | rl0n.pk0078.b9 |
| rlr48 | Resistant Rice Leaf 15 Days After Germination, 48 Hours After Infection of Strain *Magaporthe grisea* 4360-R-62 (AVR2-YAMO) | rlr48.pk0037.f4 |
| ses8w | Soybean Mature Embryo 8 Weeks After Subculture | ses8w.pk0017.c6 |
| sfl1 | Soybean Immature Flower | sfl1.pk0060.c4 |
| srr1c | Soybean 8 Day Old Root | srr1c.pk001.p10 |
| wl1n | Wheat Leaf From 7 Day Old Seedling Light Grown* | wl1n.pk0060.b11 |
| wlm12 | Wheat Seedling 12 Hours After Inoculation With *Erysiphe graminis f.* sp *tritici* | wlm12.pk0015.d7 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding aminolevulinic acid biosynthetic enzyme were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Glu-tRNA Reductase

The BLASTX search using the EST sequences from clones p0008.cb31k05r, rlr48.pk0037.f4, sfl1.pk0060.c4, srr1c.pk001.p10, and ses8w.pk0017.c6 revealed similarity of the proteins encoded by the cDNAs to Glu-tRNA reductase from different plant species. The BLAST results for each of these ESTs are shown in Table 3:

TABLE 3

BLAST Results for Clones Encoding Polypeptides Homologous to Glu-tRNA Reductase

| | | BLAST Results | |
|---|---|---|---|
| Clone | Organism | NCBI GenBank Identifier No. | pLog Score |
| p0008.cb3lk05r | *Oryza sativa* | 2920320 | 23.7 |
| rlr48.pk0037.f4 | *Oryza sativa* | 2920320 | 44.0 |
| sfl1.pk0060.c4 | *Glycine max* | 4324495 | 24.2 |
| srr1c.pk001.p10 | *Arabidopsis thaliana* | 1170203 | 13.0 |
| ses8w.pk0017.c6 | *Glycine max* | 4324495 | 11.5 |

The sequence of a portion of the cDNA insert from clone p0008.cb31k05r is shown in SEQ ID NO:1; the deduced amino acid sequence of this portion of the cDNA is shown in SEQ ID NO:2. The sequence of a portion of the cDNA insert from clone rlr48.pk0037.f4 is shown in SEQ ID NO:5; the deduced amino acid sequence of this portion of the cDNA is shown in SEQ ID NO:6. The sequence of a portion of the cDNA insert from clone sfl1.pk0060.c4 is shown in SEQ ID NO:9; the deduced amino acid sequence of this portion of the cDNA is shown in SEQ ID NO:10. The sequence of a portion of the cDNA insert from clone srr1c.pk001.p10 is shown in SEQ ID NO:13; the deduced amino acid sequence of this portion of the cDNA is shown in SEQ ID NO:14. The sequence of a portion of the cDNA insert from clone ses8w.pk0017.c6 is shown in SEQ ID NO:17; the deduced amino acid sequence of this portion of the cDNA is shown in SEQ ID NO:18. BLAST scores and probabilities indicate that the instant nucleic acid fragments encode portions of Glu-tRNA reductase. The sequence derived from clone p0008.cb31k05r represents the first corn sequence encoding Glu-tRNA reductase. Nucleic acids encoding Glu-tRNA reductase have been previously characterized in rice (Nakayashiki, T. and Inokuchi H. (1998), *Plant Physiol.* 117:332) and soybean (Sangwan I. and O'Brian, M. R. (1999), *Plant Physiol.* 119.593–598). Among the sequences disclosed herein, the rice Glu-tRNA reductase amino acid sequence reported in Nakayashiki T. and Inokuchi H. (1998), *Plant Physiol.* 117:332 shows the most homology with SEQ ID NO:6, with 93.1% identity over a sequence of 87 amino acids.

The sequence of the entire cDNA insert in some of the clones listed in Table 3 was determined. The BLASTX search using the EST sequences from clones listed in Table 4 revealed similarity of the polypeptides encoded by the cDNAs to Glu-tRNA reductase from *Oryza sativa* (NCBI GenBank Identifier (GI) No. 3913811), *Cucumis sativus* (NCBI GI No. 1346261), *Hordeum vulgare* (NCBI GI No. 1039332), and *Glycine max* (NCBI GI No. 4324495). Shown in Table 4 are the BLAST results for individual ESTs C("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 4

BLAST Results for Sequences Encoding Polypeptides Homologous to Glu-tRNA Reductase

| Clone | Status | BLAST Results | |
|---|---|---|---|
| | | NCBI GI No. | pLog Score |
| csc1c.pk005.i15 (FIS) | CGS | 3913811 | >254.00 |
| rlr48.pk0037.f4 | FIS | 3913811 | >254.00 |
| sfl1.pk0060.c4 (FIS) | CGS | 4324495 | >254.00 |
| srr1c.pk001.p10 | FIS | 1346261 | >254.00 |
| wl1n.pk0060.b11 | FIS | 1039332 | >254.00 |

FIGS. 1A–1B present an alignment of the amino acid sequences set forth in SEQ ID NOs:4 and 12 and the *Glycine max* sequence (NCBI GI No. 4324495; SEQ ID NO:29). The data in Table 5 represents a calculation of the percent identity of the amino acid sequences set forth in SEQ ID NOs:4 and 12 and the *Glycine max* sequence (NCBI GI No. 4324495; SEQ ID NO:29).

TABLE 5

Percent Identity of Amino Acid Sequences Deduced From the Nucleotide Sequences of cDNA Clones Encoding Polypeptides Homologous to Glu-tRNA Reductase

| SEQ ID NO. | Percent Identity to NCBI GI No. 4324495; SEQ ID NO:29 |
|---|---|
| 4 | 66.5 |
| 12 | 84.3 |

Sequence alignments and percent identity calculations were performed using the Megalign program of the LASERGENE, bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY-10). Default parameters for pairwise alignments using the Clustal method were KTUPLE I, GAP PENALTY=3, WINDOW=5 and DIAGONALS SAVED=5. Sequence alignments and BLAST scores and probabilities indicate that the nucleic acid fragments comprising the instant cDNA clones encode all or a substantial portion of a Glu-tRNA reductase. These sequences represent the first corn and wheat sequences indicated to encode Glu-tRNA reductase known to Applicant.

Example 4

Characterization of cDNA Clones Encoding GSA Aminotransferase

The BLASTX search using the EST sequences from clones r10n.pk0078.b9 and wlm12.pk0015.d7 revealed similarity of the proteins encoded by the cDNAs to GSA aminotransferase from *Hordeum vulgare* (NCBI GI No. 11170029). The BLAST results for each of these ESTs are shown in Table 6:

TABLE 6

BLAST Results for Clones Encoding Polypeptides Homologous to GSA Aminotransferase

| | | BLAST Results | |
|---|---|---|---|
| Clone | Organism | NCBI GI No. | pLog Score |
| r10n.pk0078.b9 | *Hordeum vulgare* | 1170029 | 34.2 |
| wlm12.pk0015.d7 | *Hordeum vulgare* | 1170029 | 21.0 |

The sequence of a portion of the cDNA insert from clone r10 n.pk0078.b9 is shown in SEQ ID NO:23; the deduced amino acid sequence of this portion of the cDNA is shown in SEQ ID NO:24. The sequence of a portion of the cDNA insert from clone wlm12.pk0015.d7 is shown in SEQ ID NO:27; the deduced amino acid sequence of this portion of the cDNA is shown in SEQ ID NO:28. BLAST scores and probabilities indicate that the instant nucleic acid fragments encode portions of GSA aminotransferase. These sequences represent the first rice and wheat sequences encoding GSA aminotransferase known to Applicant. A nucleic acid fragment encoding GSA aminotransferase has been previously characterized in soybean (Sangwan, I. and O'Brian, M. R. (1993), *Plant Physiol.* 102:829–834), and the amino acid sequence encoded by said nucleic acid fragment shows the most homology, among the sequences disclosed herein, to SEQ ID NO:16, with 93.8% identity over a sequence of 97 amino acids.

The sequence of the entire cDNA insert in clone r10n.pk0078.b9 listed in Table 6 was determined. Further sequencing and searching of the DuPont proprietary database allowed the identification of a corn clone encoding GSA aminotransferase. The BLASTX search using the EST sequences from clones listed in Table 7 revealed similarity of the polypeptides encoded by the cDNAs to GSA aminotransferase from *Hordeum vulgare* (NCBI GI No. 1170029). Shown in Table 7 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 7

BLAST Results for Sequences Encoding Polypeptides Homologous to GSA Aminotransferase

| Clone | Status | BLAST pLog Score NCBI GI No. 1170029 |
|---|---|---|
| cr1.pk0013.e7 | FIS | 120.00 |
| r10n.pk0078.b9 (FIS) | CGS | >254.00 |

FIGS. 2A–2B present an alignment of the amino acid sequence set forth in SEQ ID NO:26 and the *Hordeum vulgare* sequence (NCBI GI No. 1170029; SEQ ID NO:30). The data in Table 8 represents a calculation of the percent identity of the amino acid sequence set forth in SEQ ID NO:26 and the *Hordeum vulgare* sequence (NCBI GI No. 1170029; SEQ ID NO:30).

TABLE 8

Percent identity of Amino Acid Sequences Deduced From the Nucleotide Sequences of cDNA Clones Encoding Polypeptides Homologous to GSA Aminotransferase

| SEQ ID NO. | Percent Identity to NCBI GI NO. 1170029; SEQ ID NO:30 |
|---|---|
| 26 | 89.8 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode all or a substantial portion of a GSA aminotransferase. These sequences represent the first corn, rice, and wheat sequences encoding GSA aminotransferase known to Applicant.

Example 5

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) nay be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 6

Expression of Chimeric Genes in Dicot Cells

A seed-specific expression cassette composed of the promoter and transcription terminator from the gene encoding the 0 subunit of the seed storage protein phaseolin from the bean *Phaseolus vulgaris* (Doyle et al. (1986) *J. Biol. Chem* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 nm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/ml hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 $\mu$g/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 $\mu$L of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 $\mu$g/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 $\mu$L of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One $\mu$g of protein from the soluble fraction of the culture can be separated by SDS-polyacrylamide gel electrophoresis. Gels can be observed for protein bands migrating at the expected molecular weight Example 8

Evaluating Compounds for Their Ability to Inhibit the Activity of an Aminolevulinic Acid Biosynthetic Enzyme The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfite precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by lining the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fission protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for Glu-tRNA reductase are presented by Jahn, D. et al. (1991), J. Biol. Chem. 266:2542–2548. Assays for GSA aminotransferase are presented by Jahn, D. et al. (1991), J. Biol. Chem 266:161–167.

What is claimed is:

1. An isolated polynucleotide comprising:
   (a) a nucleotide sequence encoding polypeptide with Glu-tRNA Reductase activity, wherein the polypeptide has an amino acid sequence of at least 95% sequence identity, based on the Clustal method of alignment, when compared to one of SEQ ID NO:4, or
   (b) a complement of the nucleotide sequence, wherein the complement and the nucleotide sequence consist of the same number of nucleotides and are 100% complementary.

2. The polynucleotide of claim 1, wherein the amino acid sequence of the polypeptide comprises SEQ ID NO:4.

3. The polynucleotide of claim 1 wherein the nucleotide sequence comprises SEQ ID NO:3.

4. A vector comprising the polynucleotide of claim 1.

5. A recombinant DNA construct comprising the polynucleotide of claim 1 operably linked to at least one regulatory sequence.

6. A method for transforming a cell, comprising transforming a cell with the polynucleotide of claim 1.

7. A cell comprising the recombinant DNA construct of claim 5.

8. A method for producing a plant comprising transforming a plant cell with the polynucleotide of claim 1 and regenerating a plant from the transformed plant cell.

9. A plant comprising the recombinant DNA construct of claim 5.

10. A seed comprising the recombinant DNA construct of claim 5.

* * * * *

SEQUENCE LISTING

<160> NUMBER OF SEQ ID NOS: 30

<210> SEQ ID NO 1
<211> LENGTH: 312
<212> TYPE: DNA
<213> ORGANISM: Zea mays
<220> FEATURE:
<221> NAME/KEY: unsure
<222> LOCATION: (30)
<223> OTHER INFORMATION: n=a,c,g or t
<220> FEATURE:
<221> NAME/KEY: unsure
<222> LOCATION: (247)
<223> OTHER INFORMATION: n=a,c,g or t
<220> FEATURE:
<221> NAME/KEY: unsure
<222> LOCATION: (256)
<223> OTHER INFORMATION: n=a,c,g or t
<220> FEATURE:
<221> NAME/KEY: unsure
<222> LOCATION: (262)
<223> OTHER INFORMATION: n=a,c,g or t
<220> FEATURE:
<221> NAME/KEY: unsure
<222> LOCATION: (308)
<223> OTHER INFORMATION: n=a,c,g or t
<220> FEATURE:
<221> NAME/KEY: unsure
<222> LOCATION: (312)
<223> OTHER INFORMATION: n=a,c,g or t

<400> SEQUENCE: 1
ccaggcgcag gccttggcaa aggctgccan cgtcgccgcc ctcgagcagt tcaagatatc      60
cgccgaccgg tacatgaagg aaaggagtac catagctgtg ataggcctca gtgtacacac    120
agcaccagtg gagatggcgt gtaaaaactt gctgttgcag aggaactgtg gccccgagct    180
attcaagaac tttactagcc tgaaccatat tgaagagggc tgctgttgct tgagtgacct    240
gtgattngaa ttgganaatt tnatgtggtg ggcgctatcc atgggaaccg tggttatcag    300
agaaagtnag tn                                                       312

<210> SEQ ID NO 2
<211> LENGTH: 63
<212> TYPE: PRT
<213> ORGANISM: Zea mays
<220> FEATURE:
<221> NAME/KEY: UNSURE
<222> LOCATION: (10)
<223> OTHER INFORMATION: Xaa = ANY AMINO ACID
<220> FEATURE:
<221> NAME/KEY: UNSURE
<222> LOCATION: (46)..(47)
<223> OTHER INFORMATION: Xaa = ANY AMINO ACID

<400> SEQUENCE: 2

Gln Ala Gln Ala Leu Ala Lys Ala Ala Xaa Val Ala Ala Leu Glu Gln
  1               5                  10                  15

Phe Lys Ile Ser Ala Asp Arg Tyr Met Lys Glu Arg Ser Thr Ile Ala
             20                  25                  30

Val Ile Gly Leu Ser Val His Thr Ala Pro Val Glu Met Xaa Xaa Lys
         35                  40                  45

Leu Ala Val Ala Glu Glu Leu Trp Pro Arg Ala Ile Gln Glu Leu
     50                  55                  60

<210> SEQ ID NO 3
<211> LENGTH: 1924

<212> TYPE: DNA
<213> ORGANISM: Zea mays

<400> SEQUENCE: 3

```
ccacgcgtcc gcatcaataa agaggagctt gggaagttgc caaggcctcc gatttcgcta      60
atgcgacgat aatggcgacc acgacgtcag cgaccaccgc cgccgcagca gccgccacca     120
ccgccaagcc gcggggtcg tcgtcggccc tctgccagag ggtggccggc ggcggcaggc      180
ggcgctccgg ggtggtgcgg tgcgacgccg ccggcgtgga ggcccaggcg caggccgtgg     240
caaaggctgc cagcgtcgcc gccctcgagc agttcaagat atccgccgac cggtacatga     300
aggaaaggag taccatagct gtgataggcc tcagtgtaca cacagcacca gtggagatgc     360
gtgaaaaact tgctgttgca gaggaactgt ggccccgtgc tattcaagaa ctcactagcc     420
tgaaccatat tgaagaggct gctgttctta gtacctgtaa tagaatggaa atttatgtgg     480
tggcgctatc atggaaccgt ggtatcagag aagtagtgga ctggatgtcg aagaaaagtg     540
gtattcccgc ttccgagctt agggagcacc tgttcatctt gcgaagcagt gatgccacac     600
gccatctgtt tgaggtgtca gctggccttg actctttggt tctcggtgaa ggacaaatcc     660
ttgctcaggt taaacaagtt gtgaggagtg gacagaacag tggaggcttg ggaaagaaca     720
tcgataggat gttcaaggat gcaatcactg ctggaaagcg tgtccgcagc gagaccaaca     780
tatcatctgg tgctgtttct gtcagttcag cggcggttga actggccctg atgaagcttc     840
cgaagtctga agcactgtca gctaggatgc ttctgattgg tgctggtaaa atgggaaagc     900
tagtgatcaa acatctggtt gccaaaggat gcaagaaggt tgttgtggtg aaccgctccg     960
tggaagggt ggatgctatt cgtgaggaga tgaaagatat agagatcgtg tacaggcctc    1020
tctcagacat gtatcaagct gctgctgaag ctgatgtcgt gttcaccagc accgcatctg    1080
aaacttcatt gttcgcaaaa gaacacgcag aggcactccc ccctgtctct gatactatgg    1140
gaggtgttcg cctgtttgtc gacatatctg tccccaggaa tgtcagcgca tgtgtgtctg    1200
aagttggcgc tgcacgagtg tacaatgtcg acgacttgaa agaggtggtg aagccaaca    1260
aggaggaccg gctcaggaaa gcaatggagg cgcagacaat catcaccgaa gaactgagac    1320
ggttcgaggc atggagggac tcgctggaga ccgttccgac catcaagaag ctgaggtcgt    1380
acgcggacag gatcagggcc tcggagctcg agaagtgcct gcagaaagta ggtgaggacg    1440
ccctcaccaa gaagatgagg agagccatcg aggagctgag caccggcatc gttaacaagc    1500
tcctccatgg cccgctgcag cacctgaggt gcgacggcag cgacagccgc acccttgacg    1560
agacgctcga gaacatgcac gccctcaacc ggatgttcag cctcgacatg gagaaggcga    1620
tcatcgagca gaagatcaag gccaaggtgg agaagacaca aaactgaggc caggaagcaa    1680
ttttctacc accattatct atatatatag cgtctccaat ctcattccat ttttttatcc    1740
tttcactcag tgagcccttc ccctgctcac tgtgatcgtt aactgtgtct gtgaattaga    1800
gccatggcag cgtgttgtca ataacagcaa tgtgtcccaa ttccccacag aagaaagact    1860
atatttatat gcatttattg gagcaaatag tttacttaaa aaaaaaaaaa aaaaaaaaa    1920
aaag                                                                 1924
```

<210> SEQ ID NO 4
<211> LENGTH: 531
<212> TYPE: PRT
<213> ORGANISM: Zea mays

<400> SEQUENCE: 4

-continued

```
Met Ala Thr Thr Thr Ser Ala Thr Ala Ala Ala Ala Ala Thr
 1               5                  10                  15

Thr Ala Lys Pro Arg Gly Ser Ser Ala Leu Cys Gln Arg Val Ala
              20                  25                  30

Gly Gly Gly Arg Arg Ser Gly Val Val Arg Cys Asp Ala Ala Gly
          35                  40                  45

Val Glu Ala Gln Ala Gln Ala Val Ala Lys Ala Ala Ser Val Ala Ala
     50                  55                  60

Leu Glu Gln Phe Lys Ile Ser Ala Asp Arg Tyr Met Lys Glu Arg Ser
 65                  70                  75                  80

Thr Ile Ala Val Ile Gly Leu Ser Val His Thr Ala Pro Val Glu Met
                  85                  90                  95

Arg Glu Lys Leu Ala Val Ala Glu Glu Leu Trp Pro Arg Ala Ile Gln
             100                 105                 110

Glu Leu Thr Ser Leu Asn His Ile Glu Glu Ala Ala Val Leu Ser Thr
             115                 120                 125

Cys Asn Arg Met Glu Ile Tyr Val Val Ala Leu Ser Trp Asn Arg Gly
         130                 135                 140

Ile Arg Glu Val Val Asp Trp Met Ser Lys Lys Ser Gly Ile Pro Ala
145                 150                 155                 160

Ser Glu Leu Arg Glu His Leu Phe Ile Leu Arg Ser Ser Asp Ala Thr
                 165                 170                 175

Arg His Leu Phe Glu Val Ser Ala Gly Leu Asp Ser Leu Val Leu Gly
             180                 185                 190

Glu Gly Gln Ile Leu Ala Gln Val Lys Gln Val Val Arg Ser Gly Gln
         195                 200                 205

Asn Ser Gly Gly Leu Gly Lys Asn Ile Asp Arg Met Phe Lys Asp Ala
     210                 215                 220

Ile Thr Ala Gly Lys Arg Val Arg Ser Glu Thr Asn Ile Ser Ser Gly
225                 230                 235                 240

Ala Val Ser Val Ser Ser Ala Ala Val Glu Leu Ala Leu Met Lys Leu
                 245                 250                 255

Pro Lys Ser Glu Ala Leu Ser Ala Arg Met Leu Leu Ile Gly Ala Gly
             260                 265                 270

Lys Met Gly Lys Leu Val Ile Lys His Leu Val Ala Lys Gly Cys Lys
         275                 280                 285

Lys Val Val Val Asn Arg Ser Val Glu Arg Val Asp Ala Ile Arg
     290                 295                 300

Glu Glu Met Lys Asp Ile Glu Ile Val Tyr Arg Pro Leu Ser Asp Met
305                 310                 315                 320

Tyr Gln Ala Ala Glu Ala Asp Val Val Phe Thr Ser Thr Ala Ser
                 325                 330                 335

Glu Thr Ser Leu Phe Ala Lys Glu His Ala Glu Ala Leu Pro Pro Val
             340                 345                 350

Ser Asp Thr Met Gly Gly Val Arg Leu Phe Val Asp Ile Ser Val Pro
         355                 360                 365

Arg Asn Val Ser Ala Cys Val Ser Glu Val Gly Ala Ala Arg Val Tyr
     370                 375                 380

Asn Val Asp Asp Leu Lys Glu Val Val Glu Ala Asn Lys Glu Asp Arg
385                 390                 395                 400

Leu Arg Lys Ala Met Glu Ala Gln Thr Ile Ile Thr Glu Glu Leu Arg
                 405                 410                 415

Arg Phe Glu Ala Trp Arg Asp Ser Leu Glu Thr Val Pro Thr Ile Lys
```

-continued

```
                    420                 425                 430
Lys Leu Arg Ser Tyr Ala Asp Arg Ile Arg Ala Ser Glu Leu Glu Lys
            435                 440                 445

Cys Leu Gln Lys Val Gly Glu Asp Ala Leu Thr Lys Lys Met Arg Arg
    450                 455                 460

Ala Ile Glu Glu Leu Ser Thr Gly Ile Val Asn Lys Leu Leu His Gly
465                 470                 475                 480

Pro Leu Gln His Leu Arg Cys Asp Gly Ser Asp Ser Arg Thr Leu Asp
                485                 490                 495

Glu Thr Leu Glu Asn Met His Ala Leu Asn Arg Met Phe Ser Leu Asp
            500                 505                 510

Met Glu Lys Ala Ile Ile Glu Gln Lys Ile Lys Ala Lys Val Glu Lys
        515                 520                 525

Thr Gln Asn
    530

<210> SEQ ID NO 5
<211> LENGTH: 510
<212> TYPE: DNA
<213> ORGANISM: Oryza sativa
<220> FEATURE:
<221> NAME/KEY: unsure
<222> LOCATION: (326)
<223> OTHER INFORMATION: n=a,c,g or t
<220> FEATURE:
<221> NAME/KEY: unsure
<222> LOCATION: (335)
<223> OTHER INFORMATION: n=a,c,g or t
<220> FEATURE:
<221> NAME/KEY: unsure
<222> LOCATION: (344)
<223> OTHER INFORMATION: n=a,c,g or t
<220> FEATURE:
<221> NAME/KEY: unsure
<222> LOCATION: (355)
<223> OTHER INFORMATION: n=a,c,g or t
<220> FEATURE:
<221> NAME/KEY: unsure
<222> LOCATION: (362)
<223> OTHER INFORMATION: n=a,c,g or t
<220> FEATURE:
<221> NAME/KEY: unsure
<222> LOCATION: (364)
<223> OTHER INFORMATION: n=a,c,g or t
<220> FEATURE:
<221> NAME/KEY: unsure
<222> LOCATION: (371)
<223> OTHER INFORMATION: n=a,c,g or t
<220> FEATURE:
<221> NAME/KEY: unsure
<222> LOCATION: (378)
<223> OTHER INFORMATION: n=a,c,g or t
<220> FEATURE:
<221> NAME/KEY: unsure
<222> LOCATION: (382)
<223> OTHER INFORMATION: n=a,c,g or t
<220> FEATURE:
<221> NAME/KEY: unsure
<222> LOCATION: (390)
<223> OTHER INFORMATION: n=a,c,g or t
<220> FEATURE:
<221> NAME/KEY: unsure
<222> LOCATION: (399)
<223> OTHER INFORMATION: n=a,c,g or t
<220> FEATURE:
<221> NAME/KEY: unsure
<222> LOCATION: (403)
<223> OTHER INFORMATION: n=a,c,g or t
<220> FEATURE:
<221> NAME/KEY: unsure
<222> LOCATION: (411)..(412)
```

```
<223> OTHER INFORMATION: n=a,c,g or t
<220> FEATURE:
<221> NAME/KEY: unsure
<222> LOCATION: (434)
<223> OTHER INFORMATION: n=a,c,g or t
<220> FEATURE:
<221> NAME/KEY: unsure
<222> LOCATION: (444)
<223> OTHER INFORMATION: n=a,c,g or t
<220> FEATURE:
<221> NAME/KEY: unsure
<222> LOCATION: (448)
<223> OTHER INFORMATION: n=a,c,g or t
<220> FEATURE:
<221> NAME/KEY: unsure
<222> LOCATION: (453)
<223> OTHER INFORMATION: n=a,c,g or t
<220> FEATURE:
<221> NAME/KEY: unsure
<222> LOCATION: (483)
<223> OTHER INFORMATION: n=a,c,g or t
<220> FEATURE:
<221> NAME/KEY: unsure
<222> LOCATION: (490)
<223> OTHER INFORMATION: n=a,c,g or t
<220> FEATURE:
<221> NAME/KEY: unsure
<222> LOCATION: (492)
<223> OTHER INFORMATION: n=a,c,g or t
<220> FEATURE:
<221> NAME/KEY: unsure
<222> LOCATION: (494)
<223> OTHER INFORMATION: n=a,c,g or t
<220> FEATURE:
<221> NAME/KEY: unsure
<222> LOCATION: (502)
<223> OTHER INFORMATION: n=a,c,g or t

<400> SEQUENCE: 5
tggtacccca ggcgcaggcg gtggccaagg ccgccagcgt cgccgcgctc gagcagttca      60
agatctccgc cgaccggtac atgaaggaaa gaagtagcat agcggtaata ggcctcagtg     120
tacacactgc accagtggag atgcgtgaga aacttgctgt tgcagaggaa ctatggcccc     180
gtgctatctc agaactcacc agtctgaatc atattgaaga ggttgctgtc cttaagtacc     240
tgcaatagaa tggaaatcta tgtgggtagc tttatccgtg ggaaccgtgg gattaagaga     300
agtggtaact ggatttcaaa gaaaantgga tcccncttct aacncaagga catcnatcaa     360
gntnccttga nattgatnca anagcaatcn gtttgaggna ccnccgggct nnaccttggt     420
tcttggaaaa aggnaaatct tgcncaantt aanaatttca aaaatgggca aaaaattgga     480
ggntggaaan anancattgg tnttaagggt                                      510

<210> SEQ ID NO 6
<211> LENGTH: 87
<212> TYPE: PRT
<213> ORGANISM: Oryza sativa
<220> FEATURE:
<221> NAME/KEY: UNSURE
<222> LOCATION: (76)
<223> OTHER INFORMATION: Xaa = ANY AMINO ACID

<400> SEQUENCE: 6

Gln Ala Gln Ala Val Ala Lys Ala Ala Ser Val Ala Ala Leu Glu Gln
  1               5                  10                  15

Phe Lys Ile Ser Ala Asp Arg Tyr Met Lys Glu Arg Ser Ser Ile Ala
             20                  25                  30

Val Ile Gly Leu Ser Val His Thr Ala Pro Val Glu Met Arg Glu Lys
         35                  40                  45
```

-continued

Leu Ala Val Ala Glu Glu Leu Trp Pro Arg Ala Ile Ser Glu Leu Thr
 50                  55                  60

Ser Leu Asn His Ile Glu Glu Val Ala Val Leu Xaa Leu Ser Thr Cys
 65                  70                  75                  80

Asn Arg Met Glu Ile Tyr Val
                 85

<210> SEQ ID NO 7
<211> LENGTH: 1778
<212> TYPE: DNA
<213> ORGANISM: Oryza sativa

<400> SEQUENCE: 7

| | | | | | | |
|---|---|---|---|---|---|---|
| gcacgagtgg | tacccaggc | gcaggcggtg | gccaaggccg | ccagcgtcgc | cgcgctcgag | 60 |
| cagttcaaga | tctccgccga | ccggtacatg | aaggaaagaa | gtagcatagc | ggtaataggc | 120 |
| ctcagtgtac | acactgcacc | agtggagatg | cgtgagaaac | ttgctgttgc | agaggaacta | 180 |
| tggccccgtg | ctatctcaga | actcaccagt | ctgaatcata | ttgaagaggc | tgctgttctt | 240 |
| agtacctgca | atagaatgga | aatctatgtg | gtagctttat | cgtggaaccg | tgggattaga | 300 |
| gaagtggtag | actggatgtc | aaagaaaagt | ggaatccctg | cttctgagct | cagggagcat | 360 |
| ctattcatgt | tgcgtgacag | tgatgccaca | cgccatctgt | ttgaggtatc | tgctgggctt | 420 |
| gactctttgg | ttcttggaga | agggcaaatc | cttgctcaag | ttaaacaagt | tgtcagaagt | 480 |
| gggcaaaaca | gtggaggctt | gggaaagaac | atcgatagga | tgttcaagga | tgcaatcact | 540 |
| gctggaaagc | gtgtccgctg | cgagactaac | atatcatcag | gtgctgtctc | tgtcagttca | 600 |
| gctgcagttg | aattggcctt | gatgaagctt | ccaaagtcgg | aatgcctatc | tgctaggatg | 660 |
| ctgttgattg | gtgctggcaa | gatgggaaag | ttggtggtta | acatttgat | tgccaaggga | 720 |
| tgcaagaaag | ttgttgtggt | gaaccgttca | gtggaaaggg | tggatgccat | ccgcgaagag | 780 |
| atgaaagaca | ttgagattgt | gtacaggcct | cttacagaga | tgtatgaagc | cgctgccgaa | 840 |
| gctgatgtcg | tgttcacaag | cacggcatcc | gaaacccccat | tgttcacaaa | ggagcacgca | 900 |
| gaggcgcttc | ccgctatttc | tgatgctatg | ggtggtgttc | gactctttgt | cgacatatcc | 960 |
| gtccccagaa | atgtcagcgc | ctgtgtgtct | gaagttggcc | atgcgcgagt | atacaacgtc | 1020 |
| gatgacttga | agaggttgt | ggaagccaac | aaggaggacc | ggcttaggaa | agcaatggag | 1080 |
| gcccaaacaa | tcatcaccca | agaattgaaa | cggttcgagg | catggaggga | ctcgctggag | 1140 |
| actgttccga | ctatcaagaa | gctgaggtcc | tacgccgaca | ggatcagggc | ttcggagctt | 1200 |
| gagaagtgcc | tccagaagat | cggcgaagac | gccctcacca | gaagatgag | aagatccatc | 1260 |
| gaggagctca | gcaccggcat | cgtgaacaag | cttctccacg | gcccattgca | gcacctgaga | 1320 |
| tgtgacggca | gcgacagccg | caccctcgat | gagacgctgg | agaacatgca | cgccctcaac | 1380 |
| aggatgttca | gcctcgacac | cgagaaggcg | atcattgagc | agaagatcaa | ggcgaaggtg | 1440 |
| gagaagtccc | agaactgaga | ttgaagaaga | gatttttttt | tttcagcccg | tgtatctact | 1500 |
| atgtatacta | ctaccatatc | tgtccagaca | ttctaattcc | aatttttttt | ctctctctct | 1560 |
| tgagcctttg | cttactgagc | cctcgctgag | ttggtcaaat | tgtctcgtga | attagcgcca | 1620 |
| tggctgctgc | tagagataac | taggaaaatg | ccttgtttgt | aaattactgc | atctgctgtg | 1680 |
| gcaagagctc | cattttgaag | atattatata | cacgctgttg | gtgaaataaa | atcagaagtt | 1740 |
| catcaaaaaa | aaaaaaaaaa | aaaaaaaaaa | aaaaaaaa | | | 1778 |

<210> SEQ ID NO 8

<211> LENGTH: 480
<212> TYPE: PRT
<213> ORGANISM: Oryza sativa

<400> SEQUENCE: 8

```
Gln Ala Gln Ala Val Ala Lys Ala Ala Ser Val Ala Ala Leu Glu Gln
  1               5                  10                  15

Phe Lys Ile Ser Ala Asp Arg Tyr Met Lys Glu Arg Ser Ser Ile Ala
                 20                  25                  30

Val Ile Gly Leu Ser Val His Thr Ala Pro Val Glu Met Arg Glu Lys
             35                  40                  45

Leu Ala Val Ala Glu Glu Leu Trp Pro Arg Ala Ile Ser Glu Leu Thr
         50                  55                  60

Ser Leu Asn His Ile Glu Ala Ala Val Leu Ser Thr Cys Asn Arg
 65                  70                  75                  80

Met Glu Ile Tyr Val Val Ala Leu Ser Trp Asn Arg Gly Ile Arg Glu
                 85                  90                  95

Val Val Asp Trp Met Ser Lys Lys Ser Gly Ile Pro Ala Ser Glu Leu
                100                 105                 110

Arg Glu His Leu Phe Met Leu Arg Asp Ser Asp Ala Thr Arg His Leu
            115                 120                 125

Phe Glu Val Ser Ala Gly Leu Asp Ser Leu Val Leu Gly Glu Gly Gln
        130                 135                 140

Ile Leu Ala Gln Val Lys Gln Val Val Arg Ser Gly Gln Asn Ser Gly
145                 150                 155                 160

Gly Leu Gly Lys Asn Ile Asp Arg Met Phe Lys Asp Ala Ile Thr Ala
                165                 170                 175

Gly Lys Arg Val Arg Cys Glu Thr Asn Ile Ser Ser Gly Ala Val Ser
            180                 185                 190

Val Ser Ser Ala Ala Val Glu Leu Ala Leu Met Lys Leu Pro Lys Ser
        195                 200                 205

Glu Cys Leu Ser Ala Arg Met Leu Leu Ile Gly Ala Gly Lys Met Gly
    210                 215                 220

Lys Leu Val Val Lys His Leu Ile Ala Lys Gly Cys Lys Lys Val Val
225                 230                 235                 240

Val Val Asn Arg Ser Val Glu Arg Val Asp Ala Ile Arg Glu Glu Met
                245                 250                 255

Lys Asp Ile Glu Ile Val Tyr Arg Pro Leu Thr Glu Met Tyr Glu Ala
            260                 265                 270

Ala Ala Glu Ala Asp Val Val Phe Thr Ser Thr Ala Ser Glu Thr Pro
        275                 280                 285

Leu Phe Thr Lys Glu His Ala Glu Ala Leu Pro Ala Ile Ser Asp Ala
    290                 295                 300

Met Gly Gly Val Arg Leu Phe Val Asp Ile Ser Val Pro Arg Asn Val
305                 310                 315                 320

Ser Ala Cys Val Ser Glu Val Gly His Ala Arg Val Tyr Asn Val Asp
                325                 330                 335

Asp Leu Lys Glu Val Val Glu Ala Asn Lys Glu Asp Arg Leu Arg Lys
            340                 345                 350

Ala Met Glu Ala Gln Thr Ile Ile Thr Gln Glu Leu Lys Arg Phe Glu
        355                 360                 365

Ala Trp Arg Asp Ser Leu Glu Thr Val Pro Thr Ile Lys Lys Leu Arg
    370                 375                 380

Ser Tyr Ala Asp Arg Ile Arg Ala Ser Glu Leu Glu Lys Cys Leu Gln
```

-continued

```
            385                 390                 395                 400
Lys Ile Gly Glu Asp Ala Leu Thr Lys Lys Met Arg Arg Ser Ile Glu
                405                 410                 415

Glu Leu Ser Thr Gly Ile Val Asn Lys Leu Leu His Gly Pro Leu Gln
            420                 425                 430

His Leu Arg Cys Asp Gly Ser Asp Ser Arg Thr Leu Asp Glu Thr Leu
            435                 440                 445

Glu Asn Met His Ala Leu Asn Arg Met Phe Ser Leu Asp Thr Glu Lys
        450                 455                 460

Ala Ile Ile Glu Gln Lys Ile Lys Ala Lys Val Glu Lys Ser Gln Asn
465                 470                 475                 480

<210> SEQ ID NO 9
<211> LENGTH: 519
<212> TYPE: DNA
<213> ORGANISM: Glycine max
<220> FEATURE:
<223> OTHER INFORMATION: n=a,c,g or t
<220> FEATURE:
<221> NAME/KEY: unsure
<222> LOCATION: (217)
<223> OTHER INFORMATION: n=a,c,g or t
<220> FEATURE:
<221> NAME/KEY: unsure
<222> LOCATION: (241)
<223> OTHER INFORMATION: n=a,c,g or t
<220> FEATURE:
<221> NAME/KEY: unsure
<222> LOCATION: (243)
<223> OTHER INFORMATION: n=a,c,g or t
<220> FEATURE:
<221> NAME/KEY: unsure
<222> LOCATION: (301)
<223> OTHER INFORMATION: n=a,c,g or t
<220> FEATURE:
<221> NAME/KEY: unsure
<222> LOCATION: (360)
<223> OTHER INFORMATION: n=a,c,g or t
<220> FEATURE:
<221> NAME/KEY: unsure
<222> LOCATION: (373)
<223> OTHER INFORMATION: n=a,c,g or t
<220> FEATURE:
<221> NAME/KEY: unsure
<222> LOCATION: (405)
<223> OTHER INFORMATION: n=a,c,g or t
<220> FEATURE:
<221> NAME/KEY: unsure
<222> LOCATION: (412)
<223> OTHER INFORMATION: n=a,c,g or t
<220> FEATURE:
<221> NAME/KEY: unsure
<222> LOCATION: (426)
<223> OTHER INFORMATION: n=a,c,g or t
<220> FEATURE:
<221> NAME/KEY: unsure
<222> LOCATION: (439)
<223> OTHER INFORMATION: n=a,c,g or t
<220> FEATURE:
<221> NAME/KEY: unsure
<222> LOCATION: (447)
<223> OTHER INFORMATION: n=a,c,g or t
<220> FEATURE:
<221> NAME/KEY: unsure
<222> LOCATION: (515)
<223> OTHER INFORMATION: n=a,c,g or t

<400> SEQUENCE: 9
cacaactcaa tttgacaatt tcccttccc ttttgcactg ccctcctct ctctcgttga      60 aaatcttcca ttattatagg gttagggttc tcctgaatcc gcaatggccg tttcaaccac    120
```

-continued

```
tttctccggt gccaaattgg aggctctatt gctcaaatgt tcttcctcct cttcctcacc      180
accgccttca aggtcatcat tcaccacttt tcccggncaa acagaagaa ccctcattca       240
nanagggggtt attcgctgcg acgctcagcc ctctgatgca tcatctgttg ctccaaataa    300
ngccaccgct ctctccgctc ttgagcagct caagacttct gcagctgata gatatacaan    360
ggaaagaagc agnattatcg ccattgggct cagtgtgcac actgnacctg tngaaatgcg    420
tgaaanactg ccattccana agcaagnatg gcctagagta tgcagagctg tgtagtcgaa    480
tcatattgag aagagctgtt ctgagtacct gcaancgag                            519
```

<210> SEQ ID NO 10
<211> LENGTH: 25
<212> TYPE: PRT
<213> ORGANISM: Glycine max

<400> SEQUENCE: 10

```
Met Ala Val Ser Thr Thr Phe Ser Gly Ala Lys Leu Glu Ala Leu Leu
 1               5                  10                  15
Leu Lys Cys Ser Ser Ser Ser Ser Ser
            20                  25
```

<210> SEQ ID NO 11
<211> LENGTH: 2055
<212> TYPE: DNA
<213> ORGANISM: Glycine max

<400> SEQUENCE: 11

```
gcacgagcac aactcaattt gacaatttcc ccttcccttt tgcactgccc ctcctctctc      60
tcgttgaaaa tcttccatta ttatagggtt agggttctcc tgaatccgca atggccgttt    120
caaccacttt ctccggtgcc aaattggagg ctctattgct caaatgttct tcctcctctt    180
cctcaccacc gccttcaagg tcatcattca ccacttttcc cggccaaaac agaagaaccc    240
tcattcagag aggggttatt cgctgcgacg ctcagccctc tgatgcatca tctgttgctc    300
caaataatgc caccgctctc tccgctcttg agcagctcaa gacttctgca gctgatagat    360
atacaaagga agaagcagc attatcgcca ttgggctcag tgtgcacact gcacctgtgg     420
aaatgcgtga aaacttgcc attccagaag cagaatggcc tagagctatt gcagagctgt    480
gtagtctgaa tcatattgaa gaagcagctg ttctgagtac ctgcaatcga atggagatat    540
atgttcttgc cctgtcccaa catcgtggtg tcaaagaagt catggaatgg atgtcaaaaa    600
caagttctgt ccctgtttca gagcttagcc agcaccggtt tttactttac aacaatgatg    660
ccacacagca tcttttgaa gtatcagcag gtcttgactc tcttgttttg ggggaaggtc      720
aaatcctttc tcaggttaag caagttgtta agtgggaca aggagttaac ggcttttggga    780
gaaatatcag tgggctattc aagcatgcaa ttactgtcgg gaaaagggtt agaactgaga    840
ctaatattgc ttctggggca gtttctgtga gctcagctgc cgttgagttg gcctatatga    900
agttacctga agcctcacac gataatgcca ggatgttggt tattggtgct ggcaagatgg    960
gaaagcttgt gatcaaacat ttggtggcaa aggttgcaa aaagatggtg gttgtcaata    1020
gaactgagga gagagttgct gcaatacgtg aagaactgaa ggatattgag attatctaca    1080
aacccctttc agaaatgctc acctgtgctg gcgaagcaga tttagttttc accagtactg    1140
catcagaaaa cccattattc ttgaaagaac atgtcaagga ccttcctcct gcaagtcaag    1200
aagttggagg ccgtcgcttt ttcattgata tctctgttcc ccggaatgtg ggttcatgtg    1260
tctcagacct tgagtctgtg cgagtttaca atgttgacga ccttaaagag gttgtggctg    1320
```

-continued

```
ccaataaaga ggatcgccta agaaaagcaa tggaagcaca ggcaatcatt gctgaagaat    1380
ctaagcaatt cgaagcttgg agggactcac tggaaactgt tcctactatt aagaaattga    1440
gggcttatgc tgaaagaatc aggcttgctg agcttgagaa gtgcttaggt aagatgggtg    1500
atgatatacc aaagaaaacg cggagagctg tggatgacct tagtcggggt atagtgaata    1560
agttgcttca tggtccaatg caacatttaa ggtgtgatgg aacgacagc cggactctta     1620 gtgagacact ggagaacatg aatgctttga ataggatgtt caaccttgag acagaaatat    1680
ctgttttgga ggagaagatt cgagcaaagg tcgaacaaaa ccagaaatga aatctaacac    1740
caatcagact gatttatttt ctcctttaga ataagaggaa acatcctcac cttttagtat    1800
taatcatcct gcaatattta gttgcatagt tgaaacagct gaagtcctcc atgctgcgtc    1860
tgcttggcct aactcgtttg cgttttttgg gtcatgcgtt ttcactgtgt tcttccgcat    1920
ccatttgtct ttgtattata caaaatgaag tgttttggtg agcttcgtat ttacatcaaa    1980
taatattgtt ataagattgt ccccgtatcg ggaaaaaaaa aaaaaaaaaa aaaaaaaaa     2040 aaaaaaaaaa aaaaa                                                    2055
```

<210> SEQ ID NO 12
<211> LENGTH: 536
<212> TYPE: PRT
<213> ORGANISM: Glycine max

<400> SEQUENCE: 12

```
Met Ala Val Ser Thr Thr Phe Ser Gly Ala Lys Leu Glu Ala Leu Leu
  1               5                  10                  15

Leu Lys Cys Ser Ser Ser Ser Ser Pro Pro Ser Arg Ser Ser
                 20                  25                  30

Phe Thr Thr Phe Pro Gly Gln Asn Arg Arg Thr Leu Ile Gln Arg Gly
             35                  40                  45

Val Ile Arg Cys Asp Ala Gln Pro Ser Asp Ala Ser Val Ala Pro
         50                  55                  60

Asn Asn Ala Thr Ala Leu Ser Ala Leu Glu Gln Leu Lys Thr Ser Ala
 65                  70                  75                  80

Ala Asp Arg Tyr Thr Lys Glu Arg Ser Ile Ile Ala Ile Gly Leu
                 85                  90                  95

Ser Val His Thr Ala Pro Val Glu Met Arg Glu Lys Leu Ala Ile Pro
                100                 105                 110

Glu Ala Glu Trp Pro Arg Ala Ile Ala Glu Leu Cys Ser Leu Asn His
            115                 120                 125

Ile Glu Glu Ala Ala Val Leu Ser Thr Cys Asn Arg Met Glu Ile Tyr
        130                 135                 140

Val Leu Ala Leu Ser Gln His Arg Gly Val Lys Glu Val Met Glu Trp
145                 150                 155                 160

Met Ser Lys Thr Ser Ser Val Pro Val Ser Glu Leu Ser Gln His Arg
                165                 170                 175

Phe Leu Leu Tyr Asn Asn Asp Ala Thr Gln His Leu Phe Glu Val Ser
            180                 185                 190

Ala Gly Leu Asp Ser Leu Val Leu Gly Glu Gly Gln Ile Leu Ser Gln
        195                 200                 205

Val Lys Gln Val Val Lys Val Gly Gln Gly Val Asn Gly Phe Gly Arg
    210                 215                 220

Asn Ile Ser Gly Leu Phe Lys His Ala Ile Thr Val Gly Lys Arg Val
225                 230                 235                 240
```

```
Arg Thr Glu Thr Asn Ile Ala Ser Gly Ala Val Ser Val Ser Ser Ala
                245                 250                 255

Ala Val Glu Leu Ala Tyr Met Lys Leu Pro Glu Ala Ser His Asp Asn
            260                 265                 270

Ala Arg Met Leu Val Ile Gly Ala Gly Lys Met Gly Lys Leu Val Ile
        275                 280                 285

Lys His Leu Val Ala Lys Gly Cys Lys Met Val Val Asn Arg
290                 295                 300

Thr Glu Glu Arg Val Ala Ala Ile Arg Glu Leu Lys Asp Ile Glu
305                 310                 315                 320

Ile Ile Tyr Lys Pro Leu Ser Glu Met Leu Thr Cys Ala Gly Glu Ala
                325                 330                 335

Asp Leu Val Phe Thr Ser Thr Ala Ser Glu Asn Pro Leu Phe Leu Lys
            340                 345                 350

Glu His Val Lys Asp Leu Pro Pro Ala Ser Gln Glu Val Gly Gly Arg
        355                 360                 365

Arg Phe Phe Ile Asp Ile Ser Val Pro Arg Asn Val Gly Ser Cys Val
    370                 375                 380

Ser Asp Leu Glu Ser Val Arg Val Tyr Asn Val Asp Asp Leu Lys Glu
385                 390                 395                 400

Val Val Ala Ala Asn Lys Glu Asp Arg Leu Arg Lys Ala Met Glu Ala
                405                 410                 415

Gln Ala Ile Ile Ala Glu Glu Ser Lys Gln Phe Glu Ala Trp Arg Asp
            420                 425                 430

Ser Leu Glu Thr Val Pro Thr Ile Lys Lys Leu Arg Ala Tyr Ala Glu
        435                 440                 445

Arg Ile Arg Leu Ala Glu Leu Glu Lys Cys Leu Gly Lys Met Gly Asp
    450                 455                 460

Asp Ile Pro Lys Lys Thr Arg Arg Ala Val Asp Asp Leu Ser Arg Gly
465                 470                 475                 480

Ile Val Asn Lys Leu Leu His Gly Pro Met Gln His Leu Arg Cys Asp
                485                 490                 495

Gly Asn Asp Ser Arg Thr Leu Ser Glu Thr Leu Glu Asn Met Asn Ala
            500                 505                 510

Leu Asn Arg Met Phe Asn Leu Glu Thr Glu Ile Ser Val Leu Glu Glu
        515                 520                 525

Lys Ile Arg Ala Lys Val Glu Gln
    530                 535

<210> SEQ ID NO 13
<211> LENGTH: 507
<212> TYPE: DNA
<213> ORGANISM: Glycine max
<220> FEATURE:
<221> NAME/KEY: unsure
<222> LOCATION: (496)
<223> OTHER INFORMATION: n=a,c,g or t
<220> FEATURE:
<221> NAME/KEY: unsure
<222> LOCATION: (500)
<223> OTHER INFORMATION: n=a,c,g or t

<400> SEQUENCE: 13
ccattcttct cattgaaaaa actctcgtta ttcattgcac cacattctta ttttattttt      60
ccattcattc cttcaccaac tcccatggcg gccgtcggtg gatcctccgc cgccgccacc    120
acctcctcct ccctcttctc ctccgcccga ttccgccact ccctccgccc accgccttct    180
```

-continued

| | |
|---|---|
| caactcttct tcccacgcgc gcgcttttcc gtcaacgcca cgtgtccctt cttctccgat | 240 |
| aacaacaatt cccttcccca aaacgtcgtc gcttccaaac cctcccctct cgagttgctc | 300 |
| aaagcttcct ccgccgacag atatacgaag gaaaagagtt gcattatttg catagggctg | 360 |
| aacattcaca ctgctcccgt tgagatgcgt gagaagcttg caattccaag aatcccattg | 420 |
| ggctcaggct attaaggacc tttgcgcttt gaaccatatc gaagaagcgc gggtctaaga | 480 |
| agtggtaacg caaggngatn tatgttg | 507 |

<210> SEQ ID NO 14
<211> LENGTH: 46
<212> TYPE: PRT
<213> ORGANISM: Glycine max

<400> SEQUENCE: 14

Ala Ser Lys Pro Ser Pro Leu Glu Leu Leu Lys Ala Ser Ser Ala Asp
 1               5                  10                  15

Arg Tyr Thr Lys Glu Lys Ser Cys Ile Ile Cys Ile Gly Leu Asn Ile
            20                  25                  30

His Thr Ala Pro Val Glu Met Arg Glu Lys Leu Ala Ile Pro
        35                  40                  45

<210> SEQ ID NO 15
<211> LENGTH: 1983
<212> TYPE: DNA
<213> ORGANISM: Glycine max

<400> SEQUENCE: 15

| | |
|---|---|
| gcacgagcca ttcttctcat tgaaaaaact ctcgttattc attgcaccac attcttattt | 60 |
| ttattttcca ttcattcctt caccaactcc catggcggcc gtcggtggat cctccgccgc | 120 |
| cgccaccacc tcctcctccc tcttctcctc cgcccgattc cgccactccc tccgcccacc | 180 |
| gccttctcaa ctcttcttcc cacgcgcgcg cttttccgtc aacgccacgt gtcccttctt | 240 |
| ctccgataac aacaattccc ttccccaaaa cgtcgtcgct tccaaaccct cccctctcga | 300 |
| gttgctcaaa gcttcctccg ccgacagata tacgaaggaa aagagttgca ttatttgcat | 360 |
| agggctgaac attcacactg ctcccgttga tgcgtgag aagcttgcaa ttccagaatc | 420 |
| ccattgggct caggctatta aggacctttg cgctttgaac catatcgaag aagccgcggt | 480 |
| tctcagcacg tgtaaccgca tggagatcta tgttgtggct ctttcccagc accgtggtgt | 540 |
| taaggaagtt actgattgga tgtctaaggt gagcgggatt caatacctg agctttgtga | 600 |
| gcaccaagtt ttgctgtata acgcggatgt cacgcagcat ctctttgaag tggcggcagg | 660 |
| gcttgactca cttgttcttg ggaaggtca aattcttgct caggtgaagc aggttgtgaa | 720 |
| agctggacag ggagtgcctg gttttgataa gaaaattagt ggtttgttca gcaggcgat | 780 |
| ctcggttggg aagcgggtta gaactgagac taacatttcg tctggatcgg tttctgtcag | 840 |
| ctcggctgct gtggagctcg cactgatgaa gcttccggat cctcctttg ctgattctgg | 900 |
| agtgttggtg gttggtgcag ggaagatggg gaagcttgta attaagcatt tggctgccaa | 960 |
| agggtgcaga agaatggttg ttgttaacag gactgaagag aaagttaatg ccattcggaa | 1020 |
| agagttgaag gatgttgaga ttgtatttag accattttca gatatgctgg cgtgtgctgc | 1080 |
| tgaagctgat gtgatcttca ccagcacagc gtctgaatca ccattgtttt ctaaacagaa | 1140 |
| tgtgcagatg cttcctctgg ttaatcatgg gagaaggcgg cttttttgttg atatatctat | 1200 |
| tcctaggaat gtggaaccgg gtgtctcaga tctggagact gcacttgtgt acaatgtgga | 1260 |

-continued

```
tgatctgaag gaagttgttg cagctaacaa ggaggacagg cttcagaaag ctgaggaagc    1320
ccggggaatt atactagagg agttgaataa attcgaagct tggaaagact ctctggaaac    1380
tgttcctact attaagaagt ttagagctta tgttgagagg ataagagcct ctgagatgga    1440
gaagtgtttg tcgaagatgg gtcctgatgt ctcaaagcaa cagaaagatg caatttatgc    1500
ccttagtatg ggtattgtga ataagctact tcatggtccc atgcagcacc taaggtgtga    1560
tgggaaaaat gatagtagtc tgagtgaggt acttgagaat atgcgtgccc ttaacagaat    1620
gtacgatctt gagacagaaa tttccttgat cgaagaaaag atcagagtca agatggaacg    1680
ggttcagaag tagattcttc ttcaattggt ttagttttat ttgattcttg tggggctgc     1740 aaccctcgcc attttgtaca ctacaatagt agattgaggc cctatgaagg ctaattttt    1800 caattatttt taacattatg cagaagtaat tggacatcga tagtccaatt gaattcaaca    1860 tgtattttc tcaatgagcc tgatatagat cagttgtaaa ttcatgatcc tcatgacaac     1920
agatgattct tgtttttaa taacattaat gttagagcgg agtataaaaa aaaaaaaaa     1980 aaa                                                                 1983
```

<210> SEQ ID NO 16
<211> LENGTH: 467
<212> TYPE: PRT
<213> ORGANISM: Glycine max

<400> SEQUENCE: 16

```
Ser Pro Leu Glu Leu Leu Lys Ala Ser Ser Ala Asp Arg Tyr Thr Lys
  1               5                  10                  15

Glu Lys Ser Cys Ile Ile Cys Ile Gly Leu Asn Ile His Thr Ala Pro
             20                  25                  30

Val Glu Met Arg Glu Lys Leu Ala Ile Pro Glu Ser His Trp Ala Gln
         35                  40                  45

Ala Ile Lys Asp Leu Cys Ala Leu Asn His Ile Glu Glu Ala Ala Val
     50                  55                  60

Leu Ser Thr Cys Asn Arg Met Glu Ile Tyr Val Val Ala Leu Ser Gln
 65                  70                  75                  80

His Arg Gly Val Lys Glu Val Thr Asp Trp Met Ser Lys Val Ser Gly
                 85                  90                  95

Ile Ser Ile Pro Glu Leu Cys Glu His Gln Val Leu Leu Tyr Asn Ala
            100                 105                 110

Asp Val Thr Gln His Leu Phe Glu Val Ala Ala Gly Leu Asp Ser Leu
        115                 120                 125

Val Leu Gly Glu Gly Gln Ile Leu Ala Gln Val Lys Gln Val Val Lys
    130                 135                 140

Ala Gly Gln Gly Val Pro Gly Phe Asp Lys Lys Ile Ser Gly Leu Phe
145                 150                 155                 160

Lys Gln Ala Ile Ser Val Gly Lys Arg Val Arg Thr Glu Thr Asn Ile
                165                 170                 175

Ser Ser Gly Ser Val Ser Val Ser Ala Ala Val Glu Leu Ala Leu
            180                 185                 190

Met Lys Leu Pro Asp Ser Ser Phe Ala Asp Ser Gly Val Leu Val Val
        195                 200                 205

Gly Ala Gly Lys Met Gly Lys Leu Val Ile Lys His Leu Ala Ala Lys
    210                 215                 220

Gly Cys Arg Arg Met Val Val Val Asn Arg Thr Glu Glu Lys Val Asn
225                 230                 235                 240
```

```
Ala Ile Arg Lys Glu Leu Lys Asp Val Glu Ile Val Phe Arg Pro Phe
                245                 250                 255
Ser Asp Met Leu Ala Cys Ala Ala Glu Ala Asp Val Ile Phe Thr Ser
            260                 265                 270
Thr Ala Ser Glu Ser Pro Leu Phe Ser Lys Gln Asn Val Gln Met Leu
        275                 280                 285
Pro Leu Val Asn His Gly Arg Arg Leu Phe Val Asp Ile Ser Ile
    290                 295                 300
Pro Arg Asn Val Glu Pro Gly Val Ser Asp Leu Glu Thr Ala Leu Val
305                 310                 315                 320
Tyr Asn Val Asp Asp Leu Lys Glu Val Ala Ala Asn Lys Glu Asp
                325                 330                 335
Arg Leu Gln Lys Ala Glu Ala Arg Gly Ile Ile Leu Glu Leu
            340                 345                 350
Asn Lys Phe Glu Ala Trp Lys Asp Ser Leu Glu Thr Val Pro Thr Ile
        355                 360                 365
Lys Lys Phe Arg Ala Tyr Val Glu Arg Ile Arg Ala Ser Glu Met Glu
    370                 375                 380
Lys Cys Leu Ser Lys Met Gly Pro Asp Val Ser Lys Gln Gln Lys Asp
385                 390                 395                 400
Ala Ile Tyr Ala Leu Ser Met Gly Ile Val Asn Lys Leu Leu His Gly
                405                 410                 415
Pro Met Gln His Leu Arg Cys Asp Gly Lys Asn Asp Ser Ser Leu Ser
            420                 425                 430
Glu Val Leu Glu Asn Met Arg Ala Leu Asn Arg Met Tyr Asp Leu Glu
        435                 440                 445
Thr Glu Ile Ser Leu Ile Glu Glu Lys Ile Arg Val Lys Met Glu Arg
    450                 455                 460
Val Gln Lys
465

<210> SEQ ID NO 17
<211> LENGTH: 468
<212> TYPE: DNA
<213> ORGANISM: Glycine max
<220> FEATURE:
<221> NAME/KEY: unsure
<222> LOCATION: (1)..(2)
<223> OTHER INFORMATION: n=a,c,g or t
<220> FEATURE:
<221> NAME/KEY: unsure
<222> LOCATION: (5)
<223> OTHER INFORMATION: n=a,c,g or t
<220> FEATURE:
<221> NAME/KEY: unsure
<222> LOCATION: (8)
<223> OTHER INFORMATION: n=a,c,g or t
<220> FEATURE:
<221> NAME/KEY: unsure
<222> LOCATION: (16)
<223> OTHER INFORMATION: n=a,c,g or t
<220> FEATURE:
<221> NAME/KEY: unsure
<222> LOCATION: (18)
<223> OTHER INFORMATION: n=a,c,g or t
<220> FEATURE:
<221> NAME/KEY: unsure
<222> LOCATION: (21)..(22)
<223> OTHER INFORMATION: n=a,c,g or t
<220> FEATURE:
<221> NAME/KEY: unsure
<222> LOCATION: (27)
<223> OTHER INFORMATION: n=a,c,g or t
```

```
<220> FEATURE:
<221> NAME/KEY: unsure
<222> LOCATION: (33)
<223> OTHER INFORMATION: n=a,c,g or t
<220> FEATURE:
<221> NAME/KEY: unsure
<222> LOCATION: (35)
<223> OTHER INFORMATION: n=a,c,g or t
<220> FEATURE:
<221> NAME/KEY: unsure
<222> LOCATION: (40)
<223> OTHER INFORMATION: n=a,c,g or t
<220> FEATURE:
<221> NAME/KEY: unsure
<222> LOCATION: (101)
<223> OTHER INFORMATION: n=a,c,g or t
<220> FEATURE:
<221> NAME/KEY: unsure
<222> LOCATION: (232)
<223> OTHER INFORMATION: n=a,c,g or t
<220> FEATURE:
<221> NAME/KEY: unsure
<222> LOCATION: (298)
<223> OTHER INFORMATION: n=a,c,g or t
<220> FEATURE:
<221> NAME/KEY: unsure
<222> LOCATION: (313)
<223> OTHER INFORMATION: n=a,c,g or t
<220> FEATURE:
<221> NAME/KEY: unsure
<222> LOCATION: (349)
<223> OTHER INFORMATION: n=a,c,g or t
<220> FEATURE:
<221> NAME/KEY: unsure
<222> LOCATION: (360)
<223> OTHER INFORMATION: n=a,c,g or t
<220> FEATURE:
<221> NAME/KEY: unsure
<222> LOCATION: (377)..(378)
<223> OTHER INFORMATION: n=a,c,g or t
<220> FEATURE:
<221> NAME/KEY: unsure
<222> LOCATION: (384)
<223> OTHER INFORMATION: n=a,c,g or t
<220> FEATURE:
<221> NAME/KEY: unsure
<222> LOCATION: (388)
<223> OTHER INFORMATION: n=a,c,g or t
<220> FEATURE:
<221> NAME/KEY: unsure
<222> LOCATION: (391)..(392)
<223> OTHER INFORMATION: n=a,c,g or t
<220> FEATURE:
<221> NAME/KEY: unsure
<222> LOCATION: (397)
<223> OTHER INFORMATION: n=a,c,g or t
<220> FEATURE:
<221> NAME/KEY: unsure
<222> LOCATION: (400)
<223> OTHER INFORMATION: n=a,c,g or t
<220> FEATURE:
<221> NAME/KEY: unsure
<222> LOCATION: (407)
<223> OTHER INFORMATION: n=a,c,g or t
<220> FEATURE:
<221> NAME/KEY: unsure
<222> LOCATION: (410)
<223> OTHER INFORMATION: n=a,c,g or t
<220> FEATURE:
<221> NAME/KEY: unsure
<222> LOCATION: (423)..(424)..(425)..(426)..(427)..(428)
<223> OTHER INFORMATION: n=a,c,g or t
<220> FEATURE:
<221> NAME/KEY: unsure
<222> LOCATION: (431)..(432)
<223> OTHER INFORMATION: n=a,c,g or t
<220> FEATURE:
<221> NAME/KEY: unsure
<222> LOCATION: (434)
```

```
<223> OTHER INFORMATION: n=a,c,g or t
<220> FEATURE:
<221> NAME/KEY: unsure
<222> LOCATION: (440)..(441)
<223> OTHER INFORMATION: n=a,c,g or t
<220> FEATURE:
<221> NAME/KEY: unsure
<222> LOCATION: (446)
<223> OTHER INFORMATION: n=a,c,g or t
<220> FEATURE:
<221> NAME/KEY: unsure
<222> LOCATION: (451)
<223> OTHER INFORMATION: n=a,c,g or t
<220> FEATURE:
<221> NAME/KEY: unsure
<222> LOCATION: (454)..(455)
<223> OTHER INFORMATION: n=a,c,g or t

<400> SEQUENCE: 17
nngantangg tcacgngngt nngggtnctc ctnantccgn caatggccgt ttcaaccact      60
ttctccggtg cacaaattgg aggctctatt gctcaaatgt ncttcctcct cttcctcacc    120
accgccttca aggtcatcat tcaccacttt tcccggccaa acagaagaa ccctcattca     180
gagaggggtt attcgctgcg acgctcagcc ctctgatgca tcatctgttg cnccaaataa    240
tgccaccgct ctctccgctc ttgagcagct caagacttct gcagctgata gatatacnaa    300
tgaaagcagc agnattaccg ccattggggt cagtgtgcaa ctgcactgng aaatccgtgn    360
aaacttgcaa tcaggannag aatngccnga nntattnaan agtgtgngtn tgatatttaa    420
gannnnnngt nnantactgn natcgntgtg nttnngtctg cctgtaca                 468

<210> SEQ ID NO 18
<211> LENGTH: 26
<212> TYPE: PRT
<213> ORGANISM: Glycine max
<220> FEATURE:
<221> NAME/KEY: UNSURE
<222> LOCATION: (8)
<223> OTHER INFORMATION: Xaa = ANY AMINO ACID
<220> FEATURE:
<221> NAME/KEY: UNSURE
<222> LOCATION: (21)
<223> OTHER INFORMATION: Xaa = ANY AMINO ACID

<400> SEQUENCE: 18

Met Ala Val Ser Thr Thr Phe Xaa Pro Val His Lys Leu Glu Ala Leu
  1               5                  10                  15

Leu Leu Lys Cys Xaa Ser Ser Ser Ser Ser
             20                  25

<210> SEQ ID NO 19
<211> LENGTH: 1480
<212> TYPE: DNA
<213> ORGANISM: Triticum aestivum

<400> SEQUENCE: 19
gcacgaggaa aagagtagca tcgctgtaat aggcctcagt gtacacacag caccagtgga    60
catgcgtgaa aaacttgctg ttgcagagga actatggccc cgtgctattt cagaactcac   120
cagtctgaat catatcgaag aggctgctgt tctgagtacc tgcaacagaa tggaaatata   180
tgtggtggct ttatcgtgga accgtggtat tagagaagta gtagactgga tgtcaaagaa   240
aagtggaatc cctgcttccg agctgaggga gcatctcttt atgttgcgtg acagtgatgc   300
cacacgccat ctgtttgagg tatccgccgg gcttgactct ttggttcttg gagaaggaca   360
aatccttgct caagttaaac aagttgtcag aaatgggcaa aacagtggag cttgggaaa    420
```

```
gaacattgat aggatgttca aggatgcaat cacagctgga aagcgtgtcc gctgtgaaac    480
caacatatca gctggtgctg tgtctgtcag ttcagctgca gttgaattgg ccatgatgaa    540
gcttccaaag tctgaatgct tgtcagctag gatgcttttg attggtgctg caaaatggg     600
aaaattggtt gtcaaacatt tgattgccaa aggatgcaag aaggttgttg tggtgaaccg    660
ttctgtggaa agggtggatg ccattcgcca agagatgaaa gatattgaga ttgtgtacag    720
gcctcttaca gagatgtatg aagccgctgc tgaagctgat gtcgtgttca aagcaccgc     780
atctgaatcc ttattattca cgaaggagca tgcagaggcg cttcctccta tttctcttgc    840
tgtgggtggt gttcggcttt cgtcgacat  atctgtcccg aggaatgtcg gtgcctgtgt    900
atctgaggtg gagcatgcac gggtatacaa tgtcgacgac ttgaaagagg tggtggaagc    960
caataaggaa gaccgtgtga ggaaagcaat ggaggcccaa acaatcatta cccaagaact   1020
gaaacggttc gaggcatgga gggactcact ggagacggtt ccgaccatca aaaagctgag   1080
gtcgtacgcc gacaggatca gggcatccga gctcgagaag tgtctgcaga gatcggggga   1140
agacaatctc aacaagaaga tgagaaggtc catcgaggag ctgagcacgg gcatagtgaa   1200
caagctcctt cacggcccac tgcagcacct gagatgcgac ggcagcgaca gccgcaccct   1260
ggacgaaacg cttgagaaca tgcacgccct caacagaatg ttcaacctcg acacggagaa   1320
ggcggtcctt gagcagaaga tcaaggccaa ggtagagaag acccaaagct gagaccagga   1380
gacacttgcc cgtctgtata tctacttata ctgctcccag aatgtcgcta cattctaatc   1440
ccaatatttt tcttttggat cctccaaaaa aaaaaaaaa                          1480
```

<210> SEQ ID NO 20
<211> LENGTH: 454
<212> TYPE: PRT
<213> ORGANISM: Triticum aestivum

<400> SEQUENCE: 20

```
Glu Lys Ser Ser Ile Ala Val Ile Gly Leu Ser Val His Thr Ala Pro
  1               5                  10                  15

Val Asp Met Arg Glu Lys Leu Ala Val Ala Glu Leu Trp Pro Arg
                 20                  25                  30

Ala Ile Ser Glu Leu Thr Ser Leu Asn His Ile Glu Glu Ala Ala Val
             35                  40                  45

Leu Ser Thr Cys Asn Arg Met Glu Ile Tyr Val Val Ala Leu Ser Trp
         50                  55                  60

Asn Arg Gly Ile Arg Glu Val Val Asp Trp Met Ser Lys Lys Ser Gly
 65                  70                  75                  80

Ile Pro Ala Ser Glu Leu Arg Glu His Leu Phe Met Leu Arg Asp Ser
                 85                  90                  95

Asp Ala Thr Arg His Leu Phe Glu Val Ser Ala Gly Leu Asp Ser Leu
            100                 105                 110

Val Leu Gly Glu Gly Gln Ile Leu Ala Gln Val Lys Gln Val Val Arg
        115                 120                 125

Asn Gly Gln Asn Ser Gly Gly Leu Gly Lys Asn Ile Asp Arg Met Phe
    130                 135                 140

Lys Asp Ala Ile Thr Ala Gly Lys Arg Val Arg Cys Glu Thr Asn Ile
145                 150                 155                 160

Ser Ala Gly Ala Val Ser Val Ser Ser Ala Ala Val Glu Leu Ala Met
                165                 170                 175

Met Lys Leu Pro Lys Ser Glu Cys Leu Ser Ala Arg Met Leu Leu Ile
```

```
                    180                 185                 190
Gly Ala Gly Lys Met Gly Lys Leu Val Val Lys His Leu Ile Ala Lys
            195                 200                 205
Gly Cys Lys Lys Val Val Val Asn Arg Ser Val Glu Arg Val Asp
        210                 215                 220
Ala Ile Arg Gln Glu Met Lys Asp Ile Glu Ile Val Tyr Arg Pro Leu
225                 230                 235                 240
Thr Glu Met Tyr Glu Ala Ala Glu Ala Asp Val Val Phe Thr Ser
                245                 250                 255
Thr Ala Ser Glu Ser Leu Leu Phe Thr Lys Glu His Ala Glu Ala Leu
            260                 265                 270
Pro Pro Ile Ser Leu Ala Val Gly Gly Val Arg Leu Phe Val Asp Ile
        275                 280                 285
Ser Val Pro Arg Asn Val Gly Ala Cys Val Ser Glu Val Glu His Ala
    290                 295                 300
Arg Val Tyr Asn Val Asp Asp Leu Lys Glu Val Glu Ala Asn Lys
305                 310                 315                 320
Glu Asp Arg Val Arg Lys Ala Met Glu Ala Gln Thr Ile Ile Thr Gln
                325                 330                 335
Glu Leu Lys Arg Phe Glu Ala Trp Arg Asp Ser Leu Glu Thr Val Pro
            340                 345                 350
Thr Ile Lys Lys Leu Arg Ser Tyr Ala Asp Arg Ile Arg Ala Ser Glu
        355                 360                 365
Leu Glu Lys Cys Leu Gln Lys Ile Gly Glu Asp Asn Leu Asn Lys Lys
    370                 375                 380
Met Arg Arg Ser Ile Glu Glu Leu Ser Thr Gly Ile Val Asn Lys Leu
385                 390                 395                 400
Leu His Gly Pro Leu Gln His Leu Arg Cys Asp Gly Ser Asp Ser Arg
                405                 410                 415
Thr Leu Asp Glu Thr Leu Glu Asn Met His Ala Leu Asn Arg Met Phe
            420                 425                 430
Asn Leu Asp Thr Glu Lys Ala Val Leu Glu Gln Lys Ile Lys Ala Lys
        435                 440                 445
Val Glu Lys Thr Gln Ser
    450

<210> SEQ ID NO 21
<211> LENGTH: 846
<212> TYPE: DNA
<213> ORGANISM: Zea mays

<400> SEQUENCE: 21
gcacgagctt taagacccaa tcgccgcaaa ccccctctgaa atttcttatc cccctcatc      60 tgctccacct ccgacatcgc gcgagacgag caagcccaag tatggccgga gcagcagcag    120
ccgccgccgt ggcgtccggg gtctcggccc ggccggccgc gccgaggagg gcttctgcgg    180
gacgccgcgc tcggctgtcg gtggtgcggg ccgcgatatc cctcgagaag gcgagaagg     240 cgtacacggt gcagaagtcc gaggagatct tcaacgccgc caaggagctg atgcctggag    300
gtgttaattc gccggtccgt gccttcaaat ctgttggtgg gcagccagta gtgttcgact    360
ctgtaaaggg ttctcgtatg tgggatgttg atgggaatga gtacattgat tacgttggtt    420
cctggggtcc tgcaatcatc ggccatgcag atgataaggt taatgctgca ttgattgaaa    480
ctctgaagaa aggaactagc tttggtgctc catgtttgct ggagaacgta ttggctgaga    540
```

```
tggtcatctc tgccgtgcca agtatcgaaa tggtccgctt tgtcaactca gggacagaag      600
cctgcatggg agcgctccgc ctcgtgcgcg cattcaccgg gcgggagaag atcatcaagt      660
tcgaaggctg ctaccatggc catgccgatt ccttccttgt caaagctggc agtggtgtcg      720
ccacccttgg cctcccagac tccctggcg tccccaaggg ggccacctac gagactctaa       780 cggcaccta caatgatgtc gaggcagtga agaaactgtt cgaggacaac gcggggaga        840 ttgctg                                                                 846
```

<210> SEQ ID NO 22
<211> LENGTH: 248
<212> TYPE: PRT
<213> ORGANISM: Zea mays

<400> SEQUENCE: 22

```
Met Ala Gly Ala Ala Ala Ala Ala Val Ala Ser Gly Val Ser Ala
  1               5                  10                  15

Arg Pro Ala Ala Pro Arg Ala Ser Ala Gly Arg Arg Ala Arg Leu
                 20                  25                  30

Ser Val Val Arg Ala Ala Ile Ser Leu Glu Lys Gly Glu Lys Ala Tyr
             35                  40                      45

Thr Val Gln Lys Ser Glu Glu Ile Phe Asn Ala Ala Lys Glu Leu Met
 50                      55                      60

Pro Gly Gly Val Asn Ser Pro Val Arg Ala Phe Lys Ser Val Gly Gly
 65                  70                  75                  80

Gln Pro Val Val Phe Asp Ser Val Lys Gly Ser Arg Met Trp Asp Val
                 85                  90                  95

Asp Gly Asn Glu Tyr Ile Asp Tyr Val Gly Ser Trp Gly Pro Ala Ile
                100                 105                 110

Ile Gly His Ala Asp Asp Lys Val Asn Ala Ala Leu Ile Glu Thr Leu
            115                 120                 125

Lys Lys Gly Thr Ser Phe Gly Ala Pro Cys Leu Leu Glu Asn Val Leu
130                 135                 140

Ala Glu Met Val Ile Ser Ala Val Pro Ser Ile Glu Met Val Arg Phe
145                 150                 155                 160

Val Asn Ser Gly Thr Glu Ala Cys Met Gly Ala Leu Arg Leu Val Arg
                165                 170                 175

Ala Phe Thr Gly Arg Glu Lys Ile Ile Lys Phe Glu Gly Cys Tyr His
            180                 185                 190

Gly His Ala Asp Ser Phe Leu Val Lys Ala Gly Ser Gly Val Ala Thr
        195                 200                 205

Leu Gly Leu Pro Asp Ser Pro Gly Val Pro Lys Gly Ala Thr Tyr Glu
    210                 215                 220

Thr Leu Thr Ala Pro Tyr Asn Asp Val Glu Ala Val Lys Lys Leu Phe
225                 230                 235                 240

Glu Asp Asn Ala Gly Glu Ile Ala
                245
```

<210> SEQ ID NO 23
<211> LENGTH: 461
<212> TYPE: DNA
<213> ORGANISM: Oryza sativa
<220> FEATURE:
<221> NAME/KEY: unsure
<222> LOCATION: (136)
<223> OTHER INFORMATION: n=a,c,g or t
<220> FEATURE:
<221> NAME/KEY: unsure

```
<222> LOCATION: (220)
<223> OTHER INFORMATION: n=a,c,g or t
<220> FEATURE:
<221> NAME/KEY: unsure
<222> LOCATION: (266)
<223> OTHER INFORMATION: n=a,c,g or t
<220> FEATURE:
<221> NAME/KEY: unsure
<222> LOCATION: (334)
<223> OTHER INFORMATION: n=a,c,g or t
<220> FEATURE:
<221> NAME/KEY: unsure
<222> LOCATION: (341)
<223> OTHER INFORMATION: n=a,c,g or t
<220> FEATURE:
<221> NAME/KEY: unsure
<222> LOCATION: (348)
<223> OTHER INFORMATION: n=a,c,g or t
<220> FEATURE:
<221> NAME/KEY: unsure
<222> LOCATION: (353)
<223> OTHER INFORMATION: n=a,c,g or t
<220> FEATURE:
<221> NAME/KEY: unsure
<222> LOCATION: (356)
<223> OTHER INFORMATION: n=a,c,g or t
<220> FEATURE:
<221> NAME/KEY: unsure
<222> LOCATION: (360)
<223> OTHER INFORMATION: n=a,c,g or t
<220> FEATURE:
<221> NAME/KEY: unsure
<222> LOCATION: (382)
<223> OTHER INFORMATION: n=a,c,g or t
<220> FEATURE:
<221> NAME/KEY: unsure
<222> LOCATION: (385)
<223> OTHER INFORMATION: n=a,c,g or t
<220> FEATURE:
<221> NAME/KEY: unsure
<222> LOCATION: (396)
<223> OTHER INFORMATION: n=a,c,g or t
<220> FEATURE:
<221> NAME/KEY: unsure
<222> LOCATION: (404)
<223> OTHER INFORMATION: n=a,c,g or t
<220> FEATURE:
<221> NAME/KEY: unsure
<222> LOCATION: (410)
<223> OTHER INFORMATION: n=a,c,g or t
<220> FEATURE:
<221> NAME/KEY: unsure
<222> LOCATION: (416)
<223> OTHER INFORMATION: n=a,c,g or t
<220> FEATURE:
<221> NAME/KEY: unsure
<222> LOCATION: (419)
<223> OTHER INFORMATION: n=a,c,g or t
<220> FEATURE:
<221> NAME/KEY: unsure
<222> LOCATION: (434)
<223> OTHER INFORMATION: n=a,c,g or t
<220> FEATURE:
<221> NAME/KEY: unsure
<222> LOCATION: (451)
<223> OTHER INFORMATION: n=a,c,g or t
<220> FEATURE:
<221> NAME/KEY: unsure
<222> LOCATION: (453)
<223> OTHER INFORMATION: n=a,c,g or t

<400> SEQUENCE: 23
cttacaaaag catggccgga gcagcagccg cctccgccgc cgccgccgcc gtggcgtccg      60
ggatctcggc ccggccggtg gccccgaggc cctctccctc gcgcgcgcgc gccccacggt     120
ccgtcgtgcg ggcggncatc tccgtcgaga agggggagaa ggcgtacacg gtggagaagt     180
```

```
ccgaggagat cttcaacgcc gccaaggagt tgatgcctgn gggtgttaat tcaccagttc      240
gtgccttcaa atcagttggt gggcanccca ttgtgtttga ttctgtgaag ggtctcgtat      300
gtgggatgtg gatggaaatg aatatatcga ttangttggg ntcctgangg tcntgngatn      360
atcgggtcat gcagatgata cngtnaatgc agcatnattg aacncaaaaa aaaganctnc      420
tttgggcccc atgntatggc atgtttggtt nanaggtaac t                         461
```

```
<210> SEQ ID NO 24
<211> LENGTH: 100
<212> TYPE: PRT
<213> ORGANISM: Oryza sativa
<220> FEATURE:
<221> NAME/KEY: UNSURE
<222> LOCATION: (32)
<223> OTHER INFORMATION: Xaa = ANY AMINO ACID
<220> FEATURE:
<221> NAME/KEY: UNSURE
<222> LOCATION: (60)
<223> OTHER INFORMATION: Xaa = ANY AMINO ACID
<220> FEATURE:
<221> NAME/KEY: UNSURE
<222> LOCATION: (75)
<223> OTHER INFORMATION: Xaa = ANY AMINO ACID
<220> FEATURE:
<221> NAME/KEY: UNSURE
<222> LOCATION: (80)
<223> OTHER INFORMATION: Xaa = ANY AMINO ACID
<220> FEATURE:
<221> NAME/KEY: UNSURE
<222> LOCATION: (98)
<223> OTHER INFORMATION: Xaa = ANY AMINO ACID

<400> SEQUENCE: 24

Ala Ala Ala Val Ala Ser Gly Ile Ser Ala Arg Pro Val Ala Pro Arg
 1               5                  10                  15

Pro Ser Pro Ser Arg Ala Arg Ala Pro Arg Ser Val Val Arg Ala Xaa
                20                  25                  30

Ile Ser Val Glu Lys Gly Glu Lys Ala Tyr Thr Val Glu Lys Ser Glu
            35                  40                  45

Glu Ile Phe Asn Ala Ala Lys Glu Leu Met Pro Xaa Gly Val Asn Ser
     50                  55                  60

Pro Val Arg Ala Phe Lys Ser Val Gly Gly Xaa Pro Ile Val Phe Xaa
 65                  70                  75                  80

Phe Cys Glu Gly Ser Arg Met Trp Asp Val Asp Gly Asn Glu Tyr Ile
                85                  90                  95

Asp Xaa Val Gly
            100
```

```
<210> SEQ ID NO 25
<211> LENGTH: 1643
<212> TYPE: DNA
<213> ORGANISM: Oryza sativa

<400> SEQUENCE: 25
gcacgagctt acaaaagcat ggccggagca gcagccgcct ccgccgccgc cgccgccgtg      60
gcgtccggga tctcggcccg gccggtggcc ccgaggccct ctccctcgcg cgcgcgcgcc     120
ccacggtccg tcgtgcgggc ggccatctcc gtcgagaagg gggagaaggc gtacacggtg     180
gagaagtccg aggagatctt caacgccgcc aaggagttga tgcctggggg tgttaattca     240
ccagttcgtg ccttcaaatc agttggtggg cagcccattg tgtttgattc tgtgaagggt     300
tctcgtatgt gggatgtgga tggaaatgaa tatatcgatt atgttggttc ctgggtcct     360
```

-continued

```
gcgatcatcg gtcatgcaga tgatacggtg aatgcagcat tgattgaaac tctaaagaaa      420
ggaactagct ttggcgctcc atgtgtgttg gagaatgtgt tggctgagat ggtcatctct      480
gctgtaccaa gtatcgaaat ggtccgtttt gtcaattcag ggacagaagc ctgcatggga      540
gcgctgcgcc ttgtgcgtgc attcactggg agagagaaga ttctcaagtt tgaaggttgt      600
taccatggcc atgcagattc cttccttgtt aaagctggca gtggtgttgc caccttggc       660 ctcccagact cccctggagt ccccaaggga gccacatctg agactctaac ggcaccatac      720
aatgatgtcg aggcagtgaa aaactgtttt gaggagaaca aagggcagat tgctgctgtc      780
ttccttgagc ccgttgttgg caatgctggc ttcattcctc cacagcccgg ttttctgaat      840
gctctccgtg acttgacgaa acaagacggt gcacttttgg tctttgatga agtgatgacg      900
ggtttccgtt tagcttatgg tggggctcaa gaatacttcg ggatcacccc tgatgtgtca      960
acattgggaa atcatcggt cggtcttcca gttggcgctt atggtggacg taggacatc       1020 atggagatgg ttgctccagc agggccaatg taccaggcag gaaccctcag tggaaaccct     1080
ctagctatga ctgctggaat ccacacactc aagcgtctga tggagcctgg aacctacgat     1140
tacttggaca agatcactgg tgatcttgtt cgcggggtat tggacgcggg tgcgaaaact     1200
ggacatgaga tgtgtggagg acacatcagg gggatgttcg ggttcttctt caccgctggc     1260
ccagttcaca actttggtga cgcgaagaag agtgacaccg ccaagtttgg gaggttctac     1320
cggggcatgc ttgaagaagg tgtgtaccta gctccatccc agtttgaggc aggtttcacc     1380
agcttggcac acacctccca ggacatcgaa aaaccgtgg aggcagctgc gaaagttctt      1440
cgccggatat agagtcttcg acagttgagc ttagctacgg cttgtgaatc acttgctatt     1500
tttcatttgt gttgtacact gttagttcta catcactcaa aatctgtatt gtgcagcagc     1560
ggtacatttc ctctagcccc catatcattg tgagttagta gcatccatgg tgttttttgca   1620 gtgccaataa agttattttt gat                                              1643
```

<210> SEQ ID NO 26
<211> LENGTH: 478
<212> TYPE: PRT
<213> ORGANISM: Oryza sativa
<220> FEATURE:
<221> NAME/KEY: UNSURE
<222> LOCATION: (322)
<223> OTHER INFORMATION: Xaa = ANY AMINO ACID

<400> SEQUENCE: 26

```
Met Ala Gly Ala Ala Ala Ser Ala Ala Ala Ala Val Ala Ser
  1               5                  10                  15

Gly Ile Ser Ala Arg Pro Val Ala Pro Arg Pro Ser Pro Ser Arg Ala
                 20                  25                  30

Arg Ala Pro Arg Ser Val Val Arg Ala Ala Ile Ser Val Glu Lys Gly
             35                  40                  45

Glu Lys Ala Tyr Thr Val Glu Lys Ser Glu Glu Ile Phe Asn Ala Ala
         50                  55                  60

Lys Glu Leu Met Pro Gly Gly Val Asn Ser Pro Val Arg Ala Phe Lys
     65                  70                  75                  80

Ser Val Gly Gly Gln Pro Ile Val Phe Asp Ser Val Lys Gly Ser Arg
                 85                  90                  95

Met Trp Asp Val Asp Gly Asn Glu Tyr Ile Asp Tyr Val Gly Ser Trp
                100                 105                 110

Gly Pro Ala Ile Ile Gly His Ala Asp Asp Thr Val Asn Ala Ala Leu
            115                 120                 125
```

```
Ile Glu Thr Leu Lys Lys Gly Thr Ser Phe Gly Ala Pro Cys Val Leu
    130                 135                 140
Glu Asn Val Leu Ala Glu Met Val Ile Ser Ala Val Pro Ser Ile Glu
145                 150                 155                 160
Met Val Arg Phe Val Asn Ser Gly Thr Glu Ala Cys Met Gly Ala Leu
                165                 170                 175
Arg Leu Val Arg Ala Phe Thr Gly Arg Glu Lys Ile Leu Lys Phe Glu
            180                 185                 190
Gly Cys Tyr His Gly His Ala Asp Ser Phe Leu Val Lys Ala Gly Ser
        195                 200                 205
Gly Val Ala Thr Leu Gly Leu Pro Asp Ser Pro Gly Val Pro Lys Gly
    210                 215                 220
Ala Thr Ser Glu Thr Leu Thr Ala Pro Tyr Asn Asp Val Glu Ala Val
225                 230                 235                 240
Lys Lys Leu Phe Glu Glu Asn Lys Gly Gln Ile Ala Ala Val Phe Leu
                245                 250                 255
Glu Pro Val Val Gly Asn Ala Gly Phe Ile Pro Pro Gln Pro Gly Phe
            260                 265                 270
Leu Asn Ala Leu Arg Asp Leu Thr Lys Gln Asp Gly Ala Leu Leu Val
        275                 280                 285
Phe Asp Glu Val Met Thr Gly Phe Arg Leu Ala Tyr Gly Gly Ala Gln
    290                 295                 300
Glu Tyr Phe Gly Ile Thr Pro Asp Val Ser Thr Leu Gly Lys Ile Ile
305                 310                 315                 320
Gly Xaa Gly Leu Pro Val Gly Ala Tyr Gly Gly Arg Lys Asp Ile Met
                325                 330                 335
Glu Met Val Ala Pro Ala Gly Pro Met Tyr Gln Ala Gly Thr Leu Ser
            340                 345                 350
Gly Asn Pro Leu Ala Met Thr Ala Gly Ile His Thr Leu Lys Arg Leu
        355                 360                 365
Met Glu Pro Gly Thr Tyr Asp Tyr Leu Asp Lys Ile Thr Gly Asp Leu
    370                 375                 380
Val Arg Gly Val Leu Asp Ala Gly Ala Lys Thr Gly His Glu Met Cys
385                 390                 395                 400
Gly Gly His Ile Arg Gly Met Phe Gly Phe Phe Thr Ala Gly Pro
                405                 410                 415
Val His Asn Phe Gly Asp Ala Lys Lys Ser Asp Thr Ala Lys Phe Gly
            420                 425                 430
Arg Phe Tyr Arg Gly Met Leu Glu Glu Gly Val Tyr Leu Ala Pro Ser
        435                 440                 445
Gln Phe Glu Ala Gly Phe Thr Ser Leu Ala His Thr Ser Gln Asp Ile
    450                 455                 460
Glu Lys Thr Val Glu Ala Ala Lys Val Leu Arg Arg Ile
465                 470                 475

<210> SEQ ID NO 27
<211> LENGTH: 650
<212> TYPE: DNA
<213> ORGANISM: Triticum aestivum
<220> FEATURE:
<221> NAME/KEY: unsure
<222> LOCATION: (321)
<223> OTHER INFORMATION: n=a,c,g or t
<220> FEATURE:
<221> NAME/KEY: unsure
<222> LOCATION: (334)
```

-continued

```
<223> OTHER INFORMATION: n=a,c,g or t
<220> FEATURE:
<221> NAME/KEY: unsure
<222> LOCATION: (350)
<223> OTHER INFORMATION: n=a,c,g or t
<220> FEATURE:
<221> NAME/KEY: unsure
<222> LOCATION: (356)
<223> OTHER INFORMATION: n=a,c,g or t
<220> FEATURE:
<221> NAME/KEY: unsure
<222> LOCATION: (362)
<223> OTHER INFORMATION: n=a,c,g or t
<220> FEATURE:
<221> NAME/KEY: unsure
<222> LOCATION: (367)
<223> OTHER INFORMATION: n=a,c,g or t
<220> FEATURE:
<221> NAME/KEY: unsure
<222> LOCATION: (375)
<223> OTHER INFORMATION: n=a,c,g or t
<220> FEATURE:
<221> NAME/KEY: unsure
<222> LOCATION: (400)
<223> OTHER INFORMATION: n=a,c,g or t
<220> FEATURE:
<221> NAME/KEY: unsure
<222> LOCATION: (402)
<223> OTHER INFORMATION: n=a,c,g or t
<220> FEATURE:
<221> NAME/KEY: unsure
<222> LOCATION: (417)
<223> OTHER INFORMATION: n=a,c,g or t
<220> FEATURE:
<221> NAME/KEY: unsure
<222> LOCATION: (439)
<223> OTHER INFORMATION: n=a,c,g or t
<220> FEATURE:
<221> NAME/KEY: unsure
<222> LOCATION: (460)
<223> OTHER INFORMATION: n=a,c,g or t
<220> FEATURE:
<221> NAME/KEY: unsure
<222> LOCATION: (464)
<223> OTHER INFORMATION: n=a,c,g or t
<220> FEATURE:
<221> NAME/KEY: unsure
<222> LOCATION: (467)
<223> OTHER INFORMATION: n=a,c,g or t
<220> FEATURE:
<221> NAME/KEY: unsure
<222> LOCATION: (475)
<223> OTHER INFORMATION: n=a,c,g or t
<220> FEATURE:
<221> NAME/KEY: unsure
<222> LOCATION: (490)
<223> OTHER INFORMATION: n=a,c,g or t
<220> FEATURE:
<221> NAME/KEY: unsure
<222> LOCATION: (499)
<223> OTHER INFORMATION: n=a,c,g or t
<220> FEATURE:
<221> NAME/KEY: unsure
<222> LOCATION: (507)
<223> OTHER INFORMATION: n=a,c,g or t
<220> FEATURE:
<221> NAME/KEY: unsure
<222> LOCATION: (528)
<223> OTHER INFORMATION: n=a,c,g or t
<220> FEATURE:
<221> NAME/KEY: unsure
<222> LOCATION: (530)
<223> OTHER INFORMATION: n=a,c,g or t
<220> FEATURE:
<221> NAME/KEY: unsure
<222> LOCATION: (537)
<223> OTHER INFORMATION: n=a,c,g or t
<220> FEATURE:
<221> NAME/KEY: unsure
```

```
<222> LOCATION: (602)..(603)
<223> OTHER INFORMATION: n=a,c,g or t
<220> FEATURE:
<221> NAME/KEY: unsure
<222> LOCATION: (609)
<223> OTHER INFORMATION: n=a,c,g or t
<220> FEATURE:
<221> NAME/KEY: unsure
<222> LOCATION: (625)
<223> OTHER INFORMATION: n=a,c,g or t
<220> FEATURE:
<221> NAME/KEY: unsure
<222> LOCATION: (636)
<223> OTHER INFORMATION: n=a,c,g or t
<220> FEATURE:
<221> NAME/KEY: unsure
<222> LOCATION: (650)
<223> OTHER INFORMATION: n=a,c,g or t

<400> SEQUENCE: 27
ctaaaaccaa gtttaccaat tctcttatcc cctcctcatc ttctcccgc acccgacgac       60 atcgcgggag aaggaaggaa gcatcatggc cggagcagca gccgccgccg ccgccgtggc     120
ctccggcatc tcgatccgga cggtcgccgc tcctaagatc tcgcgcgcgc tcgctctcg     180 gtcggtggtg aagggcggcc gtttccttag gcgagaaggc ttacacggtt caagaaatct     240
gaggagattt tcaacgctgc caaaggaatt tgatgcctgg aggtgttaat tcaaccaatc     300
cgtgccttca aaatcaatcc nggcgggaac ccanaattttt tgattccgtn aaaggntctc     360
anatgtngga ttccnatgga aatgaataat tgataagttn gntcctgggg cctgcancat     420
tggtcacgca aattacaang tgaagctgca ttattgaaan ccgnaanaag gaacnactttt     480 gggccaagtn cttgggaang ttttggnaaa atggcaactc gctgtccnan tacaaanggt     540
cctttgtaaa tcaagacaaa actgatggga gaatcgcctt tcgtcatta ctggaaggaa     600 anntccaant taagggttca tgcangaaat ccttcnctta aaagaagggn              650

<210> SEQ ID NO 28
<211> LENGTH: 67
<212> TYPE: PRT
<213> ORGANISM: Triticum aestivum

<400> SEQUENCE: 28

Met Ala Gly Ala Ala Ala Ala Ala Ala Val Ala Ser Gly Ile Ser
 1               5                  10                  15

Ile Arg Thr Val Ala Ala Pro Lys Ile Ser Arg Ala Pro Arg Ser Arg
                20                  25                  30

Ser Val Val Lys Gly Gly Arg Phe Leu Arg Arg Glu Gly Leu His Gly
            35                  40                  45

Ser Arg Asn Leu Arg Arg Phe Ser Thr Leu Pro Lys Glu Phe Asp Ala
        50                  55                  60

Trp Arg Cys
 65

<210> SEQ ID NO 29
<211> LENGTH: 542
<212> TYPE: PRT
<213> ORGANISM: soybean

<400> SEQUENCE: 29

Met Ala Val Ser Thr Ser Phe Pro Gly Ala Lys Leu Glu Ala Leu Leu
 1               5                  10                  15

Leu Lys Cys Gly Ser Ser Asn Ala Ala Thr Ala Thr Ala Thr Thr Thr
                20                  25                  30
```

-continued

Thr His Leu Ser Cys Phe Cys Lys Thr Arg Lys Thr Leu Val Gln Ser
        35                  40                  45

Gln Arg Gly Pro Ile Arg Cys Glu Ala Ser Ser Ala Ser Asp Val Val
        50                  55                  60

Ala Asp Ala Thr Lys Lys Ala Ala Ser Val Ser Ala Leu Glu Gln Leu
65                  70                  75                  80

Lys Thr Ser Ala Ala Asp Arg Tyr Thr Lys Glu Arg Ser Ser Val Met
                85                  90                  95

Val Ile Gly Leu Ser Val His Ser Thr Pro Val Glu Met Arg Glu Lys
                100                 105                 110

Leu Ala Ile Pro Glu Ala Glu Trp Pro Arg Ala Ile Ala Glu Leu Cys
            115                 120                 125

Ser Leu Asn His Ile Glu Glu Ala Ala Val Leu Ser Thr Cys Asn Arg
        130                 135                 140

Met Glu Ile Tyr Val Val Ala Leu Ser Lys His Arg Gly Val Lys Glu
145                 150                 155                 160

Val Thr Glu Trp Met Ser Lys Thr Ser Gly Ile Pro Val Ala Asp Leu
                165                 170                 175

Cys Gln His Gln Phe Leu Leu Tyr Asn Lys Asp Ala Thr Gln His Leu
                180                 185                 190

Phe Glu Val Ser Ala Gly Leu Asp Ser Leu Val Leu Gly Glu Gly Gln
            195                 200                 205

Ile Leu Ala Gln Val Lys Gln Val Lys Val Gly Gln Gly Val Asn
        210                 215                 220

Gly Phe Gly Arg Asn Ile Ser Gly Leu Phe Lys His Ala Ile Thr Val
225                 230                 235                 240

Gly Lys Arg Val Arg Thr Glu Thr Asn Ile Ala Ala Gly Ala Val Ser
                245                 250                 255

Val Ser Ser Ala Ala Val Glu Leu Ala Leu Met Lys Leu Pro Glu Ala
                260                 265                 270

Ser His Ala Asn Ala Arg Met Leu Val Ile Gly Ala Gly Lys Met Gly
        275                 280                 285

Lys Leu Val Ile Lys His Leu Val Ala Lys Gly Cys Thr Lys Met Val
        290                 295                 300

Val Val Asn Arg Ser Glu Glu Arg Val Ala Ala Ile Arg Glu Glu Ile
305                 310                 315                 320

Lys Asp Val Glu Ile Ile Tyr Lys Pro Leu Ser Glu Met Leu Thr Cys
                325                 330                 335

Ile Gly Glu Ala Asp Val Val Phe Thr Ser Thr Ala Ser Glu Asn Pro
            340                 345                 350

Leu Phe Leu Lys Asp Asp Val Lys Glu Leu Pro Pro Ala Thr Asp Glu
        355                 360                 365

Val Gly Gly Arg Arg Leu Phe Val Asp Ile Ser Val Pro Arg Asn Val
        370                 375                 380

Gly Ser Cys Leu Ser Asp Leu Glu Ser Val Arg Val Tyr Asn Val Asp
385                 390                 395                 400

Asp Leu Lys Glu Val Val Ala Ala Asn Lys Glu Asp Arg Leu Arg Lys
                405                 410                 415

Ala Met Glu Ala Gln Ala Ile Ile Gly Glu Glu Ser Lys Gln Phe Glu
            420                 425                 430

Ala Trp Arg Asp Ser Leu Glu Thr Val Pro Thr Ile Lys Lys Leu Arg
        435                 440                 445

```
Ala Tyr Ala Glu Arg Ile Arg Leu Ala Glu Leu Glu Lys Cys Leu Gly
    450                 455                 460

Lys Met Gly Asp Asp Ile Asn Lys Lys Thr Gln Arg Ala Val Asp Asp
465                 470                 475                 480

Leu Ser Arg Gly Ile Val Asn Lys Leu Leu His Gly Pro Met Gln His
                485                 490                 495

Leu Arg Cys Asp Gly Ser Asp Ser Arg Thr Leu Ser Glu Thr Leu Glu
            500                 505                 510

Asn Met His Ala Leu Asn Arg Met Phe Asn Leu Glu Thr Glu Ile Ser
        515                 520                 525

Val Leu Glu Gln Lys Ile Arg Ala Lys Val Glu Gln Lys Pro
    530                 535                 540
```

<210> SEQ ID NO 30
<211> LENGTH: 469
<212> TYPE: PRT
<213> ORGANISM: [Hordeum vulgare]

<400> SEQUENCE: 30

```
Met Ala Gly Ala Ala Ala Val Ala Ser Gly Ile Ser Ile Arg Pro
1               5                   10                  15

Val Ala Ala Pro Lys Ile Ser Arg Ala Pro Arg Ser Arg Ser Val Val
                20                  25                  30

Arg Ala Ala Val Ser Ile Asp Glu Lys Ala Tyr Thr Val Gln Lys Ser
            35                  40                  45

Glu Glu Ile Phe Asn Ala Ala Lys Glu Leu Met Pro Gly Gly Val Asn
        50                  55                  60

Ser Pro Val Arg Ala Phe Lys Ser Val Gly Gly Gln Pro Ile Val Phe
65                  70                  75                  80

Asp Ser Val Lys Gly Ser His Met Trp Asp Val Asp Gly Asn Glu Tyr
                85                  90                  95

Ile Asp Tyr Val Gly Ser Trp Gly Pro Ala Ile Ile Gly His Ala Asp
                100                 105                 110

Asp Lys Val Asn Ala Ala Leu Ile Glu Thr Leu Lys Lys Gly Thr Ser
            115                 120                 125

Phe Gly Ala Pro Cys Ala Leu Glu Asn Val Leu Ala Gln Met Val Ile
        130                 135                 140

Ser Ala Val Pro Ser Ile Glu Met Val Arg Phe Val Asn Ser Gly Thr
145                 150                 155                 160

Glu Ala Cys Met Gly Ala Leu Arg Leu Val Arg Ala Phe Thr Gly Arg
                165                 170                 175

Glu Lys Ile Leu Lys Phe Glu Gly Cys Tyr His Gly His Ala Asp Ser
                180                 185                 190

Phe Leu Val Lys Ala Gly Ser Gly Val Ala Thr Leu Gly Leu Pro Asp
        195                 200                 205

Ser Pro Gly Val Pro Lys Gly Ala Thr Val Gly Thr Leu Thr Ala Pro
    210                 215                 220

Tyr Asn Asp Ala Asp Ala Val Lys Lys Leu Phe Glu Asp Asn Lys Gly
225                 230                 235                 240

Glu Ile Ala Ala Val Phe Leu Glu Pro Val Val Gly Asn Ala Gly Phe
                245                 250                 255

Ile Pro Pro Gln Pro Ala Phe Leu Asn Ala Leu Arg Glu Val Thr Lys
                260                 265                 270

Gln Asp Gly Ala Leu Leu Val Phe Asp Glu Val Met Thr Gly Phe Arg
            275                 280                 285
```

```
Leu Ala Tyr Gly Gly Ala Gln Glu Tyr Phe Gly Ile Thr Pro Asp Val
    290             295             300

Thr Thr Leu Gly Lys Ile Ile Gly Gly Gly Leu Pro Val Gly Ala Tyr
305             310             315                     320

Gly Gly Arg Lys Asp Ile Met Glu Met Val Ala Pro Ala Gly Pro Met
            325             330             335

Tyr Gln Ala Gly Thr Leu Ser Gly Asn Pro Leu Ala Met Thr Ala Gly
            340             345             350

Ile His Thr Leu Lys Arg Leu Met Glu Pro Gly Thr Tyr Glu Tyr Leu
        355             360             365

Asp Lys Val Thr Gly Glu Leu Val Arg Gly Ile Leu Asp Val Gly Ala
        370             375             380

Lys Thr Gly His Glu Met Cys Gly Gly His Ile Arg Gly Met Phe Gly
385             390             395                     400

Phe Phe Phe Ala Gly Gly Pro Val His Asn Phe Asp Asp Ala Lys Lys
            405             410             415

Ser Asp Thr Ala Lys Phe Gly Arg Phe His Arg Gly Met Leu Gly Glu
            420             425             430

Gly Val Tyr Leu Ala Pro Ser Gln Phe Glu Ala Gly Phe Thr Ser Leu
        435             440             445

Ala His Thr Thr Gln Asp Ile Glu Lys Thr Val Glu Ala Ala Glu Lys
    450             455             460

Val Leu Arg Trp Ile
465
```